United States Patent [19]

Godlewski et al.

[11] Patent Number: 5,551,428
[45] Date of Patent: Sep. 3, 1996

[54] AUTOMATIC ROUTING TO SELECTED DESTINATIONS OF STORAGE PHOSPHOR IMAGES

[75] Inventors: Wayne W. Godlewski, Hilton; James D. Chapman; Gary M. Diana, both of Henrietta; Steven P. Hiss, Fairport; Jane M. Volo, Rochester; Richard Weil, Pittsford; Lance H. Underwood, Rochester, all of N.Y.

[73] Assignee: Eastman Kodak Company, Rochester, N.Y.

[21] Appl. No.: 422,001

[22] Filed: Apr. 12, 1995

Related U.S. Application Data

[63] Continuation of Ser. No. 981,144, Nov. 24, 1992, abandoned.

[51] Int. Cl.$^6$ .................................................. A61B 5/05
[52] U.S. Cl. .................................................. 128/653.1
[58] Field of Search .................... 128/653.1; 364/413.01, 364/413.02, 413.03, 413.13

[56] References Cited

U.S. PATENT DOCUMENTS

| | | | |
|---|---|---|---|
| Re. 31,847 | 3/1985 | Luckey | 250/327.2 |
| 4,816,680 | 3/1989 | Nakajima et al. | 250/327.2 |
| 4,817,050 | 3/1989 | Komatsu et al. | 364/616.2 |
| 4,847,694 | 7/1989 | Nishihara | 358/434 |
| 4,958,283 | 9/1990 | Tawara et al. | 364/413.13 |
| 5,086,392 | 2/1992 | Nakajima | 364/413.22 |
| 5,125,075 | 6/1992 | Goodale et al. | 395/200 |
| 5,140,518 | 8/1992 | Ema | 364/413.01 |
| 5,151,592 | 9/1992 | Boutet et al. | 250/228 |
| 5,179,651 | 1/1993 | Taaffe et al. | 395/154 |
| 5,200,993 | 4/1993 | Wheeler et al. | 379/96 |
| 5,231,572 | 7/1993 | Shigyo et al. | 364/413.01 |
| 5,270,530 | 12/1993 | Godlewski et al. | 250/208.1 |
| 5,359,512 | 10/1994 | Nishihara | 364/413.01 |
| 5,404,292 | 4/1995 | Hendrickson | 364/413.02 |
| 5,446,709 | 8/1995 | Mukai | 364/413.13 |

*Primary Examiner*—Krista M. Zele
*Assistant Examiner*—Brian L. Casler
*Attorney, Agent, or Firm*—William F. Noval

[57] ABSTRACT

A laser imaging system, such as a storage phosphor system, provides an x-ray image signal. X-ray image processing apparatus includes an image processor for processing the x-ray image signal for an image parameter to produce an image processed x-ray image signal; a database for storing image parameters for producing different versions of an image processed x-ray image signal and for storing preselected destinations that each version can be sent to; and a control system for controlling the image processor and database to create multiple versions of the x-ray image signal, such that each version has different image parameter values and for routing each version to the preselected destination stored in said database.

4 Claims, 21 Drawing Sheets

QC Exams

Patient Name:
Patient ID:
Exam Date/Time:
Version:

Patient Information

Exam Information

Image Orientation

Image Processing

Route Exam

Discard Exam

Exam List

Main Menu

Exams Available for Initial QC 026-30-2277 Robins, Janet E.
045-68-0246 Hiss, Steven P.

Exams Available for Reprocessing 045-68-0246 Hiss, Steven P.
026-30-2277 Robins, Janet E.
110-52-8378 Stall, Gretchen L.

QC Exams

Patient Name: Robins, Janet E.
Patient ID: 026-30-2277
Exam Date/Time: 05-05-92
Version: ◇1 ◇2 ◇3 ◇4

Route Exam

1. Verify Exam Information:
   Tech ID: JER
   Requisition Number: xyz123
   Cassette ID: BB1023
   Projection: AP
   Body Part: Chest
   Position: Supine
   Distance: 45
   kVp: 70
   mAs: 2.5

2. Select Exam Destination(s):
   ICU1 PDS
   ICU2 PDS
   Radiology Kelp
   Archive Number of Prints: 1
Print Priority: Normal Route Exam    Modify Exam

Patient Information

Patient Name: Robins, Janet E.
Patient ID: 123-45-6789
Date of Birth: 08-10-1965
Patient Sex: Female
Radiologist: Dr. Joanne Vane
Referring Physician: Dr. Lance Underwood
Room-Unit Number: 222
Bed Number: 13

Destination(s):
ICU1 PDS
ICU2 PDS
Radiology KELP

Update  Reset  Done

QC Exams

QC Exams

Exam Information

Tech ID
JER
Requisition number
xxz123
Cassette ID
BB10234567
Projection
AP
Body Part
Chest
Position
Supine
Distance
45
kVp
70
mAs
2.5
Exposure Index
4095
Comments
1 copy to Livingstone Update  Reset  Done

FOR CHEST/ABDOMEN

|  | KERNEL SIZE | HIGH BOOST | LOW BOOST |
| --- | --- | --- | --- |
| HIGH | 75 | 1.5 | .5 |
| MEDIUM | 75 | 1 | .25 |
| LOW | 75 | .5 | .125 |

FOR EXTREMITIES

|  | KERNEL SIZE | HIGH BOOST | LOW BOOST |
| --- | --- | --- | --- |
| HIGH | 37 | 1.5 | 1.5 |
| MEDIUM | 37 | 1 | 1 |
| LOW | 37 | .5 | .5 |

FIG. 27

| EXAM TYPE | AVERAGE DENSITY | LUT START |
| --- | --- | --- |
| SKULL | 1050 | 150 |
| CERVICAL SPINE | 1050 | 150 |
| LATERAL CHEST | 1000 | 0 |
| OTHER CHEST | 950 | 0 |
| THORACIC SPINE | 950 | 0 |
| CLAVICLE | 950 | 0 |
| BREAST | 950 | 0 |
| ABDOMEN | 1050 | 150 |
| LUMBAR | 1050 | 150 |
| PELVIS | 1050 | 150 |
| HIP | 1050 | 150 |
| EXTREMITY | 1350 | 150 |

QC Exams

Patient Name: Robins, Janet E.
Patient ID: 026-30-2277
Exam Date/Time: 05-05-92
Version: ◇1 ◇2 ◇3 ◇4

WIDTH: 1250    LEVEL: 250

1. VERIFY EXAM INFORMATION:

TECH ID:         GLS
   REQUISITION NUM: 652436
   BODY PART:       CHEST
   PROJECTION:      AP
   POSITION:        SUPINE

PATIENT MOVED DURING EXPO.

2. SELECT EXAM DESTINATION(S):

POS-3RD FLOOR
   POS-CCU
   POS-PEDIATRIC
   KELP-RAD. DEPT. 1

NUMBER OF PRINTS  1
   PRINT PRIORITY    NORMAL

[ROUTE EXAM]  [MODIFY EXAM]

AUTOMATIC ROUTING TO SELECTED DESTINATIONS OF STORAGE PHOSPHOR IMAGES

This is a continuation of U.S. application Ser. No. 981,144, filed Nov. 24, 1992, now abandoned.

FIELD OF THE INVENTION

This invention relates in general to laser imaging systems and more particularly to storage phosphor systems in which a latent x-ray image is recorded in a storage phosphor. A storage phosphor reader converts the stored latent x-ray image into an x-ray image signal. The x-ray image signal is automatically routed to selected destination(s).

BACKGROUND OF THE INVENTION

Portable x-ray images are used to aid in assessing pathological changes and/or tube/line placement in critically ill patients in the U.S. Over 50% of portable examinations are performed in Critical Care Units (Intensive Care and Coronary Care). The remaining portable exams are performed on the medical or surgical floors or in the Emergency Room. Most patients in a Critical Care Unit have an x-ray procedure at least once per day. The primary portable exam type is AP (anterior-posterior) chest (80% of portable procedures) followed by abdomen and bone. The portable chest radiography market is expected to grow 20% in the United States over the next 5 years.

The technologist's problems in portable radiography are well known: maneuverability of the portable x-ray generator, carrying a large number of cassettes, x-ray tube positioning and determination of proper technique. The variability in positioning the x-ray tube results in different techniques between exams. This sometimes results in over or underexposure so that the radiologist requires an exam to be repeated. The average repeat rate is on the order of 5% to 10%.

The films that are generated while the patient is in a Critical Care Unit are kept in either the radiology department or in the unit. Typically, the most recent films are put on an alternator for easy access and review. Consultation about the procedure occurs where the films are located, requiring either the radiologist or the clinician to go to the films. At some institutions, a double film protocol is used in order to give both the radiologist and clinician easier access to the image.

As radiologists read portable exams, the most current film is compared to previous films to assess changes in the patient's condition. The variability in exposure with current film/screen combinations adds to the difficulty in the assessment of changes that are due to illness.

The clinicians in the Critical Care area often need immediate access to the portable films in order to check proper tube placement. They often "borrow" the film from the radiology department before the radiologist has a chance to read it. Sometimes these films are not returned and a report is not generated; thus the hospital has lost revenue for that exam.

As the population grows older, more people will be hospitalized and require surgery and critical care. Thus the number of portable examinations will increase; the need for better quality and faster portables will increase and hospitals will be in a position to justify the allocation of funds for new systems and additional generators specifically for portable procedures.

In the decades after the end of World War II, there were significant advances in phosphor materials. These advances made high speed electronic imaging possible. Research at Eastman Kodak Company, Rochester, N.Y., led to the first demonstration of a scanned storage phosphor radiographic system. This system was originally patented in 1975 and reissued as U.S. Pat. No. Reissue 31,847, reissued Mar. 12, 1985, to Luckey. In the storage phosphor system disclosed a storage phosphor is exposed to an x-ray image of an object, such as the body part of a patient, to record a latent x-ray image in the storage phosphor. The latent x-ray image is read out by stimulating the storage phosphor with relatively long wavelength stimulating radiation such as red or infrared light produced by a helium neon gas laser or diode laser. Upon stimulation, the storage phosphor releases emitted radiation of an intermediate wavelength, such as blue light, in proportion to the quantity of x-rays that were received. To produce a signal useful in electronic image processing the storage phosphor is scanned in a raster pattern by a laser beam deflected by an oscillating or rotating scanning mirror or hologon. The emitted radiation from the storage phosphor is reflected by a mirror light collector and detected by a photodetector such as a photomultiplier to produce an electronic x-ray image signal. Typically the storage phosphor is translated in a page scan direction past the laser beam which is repeatedly deflected in a line scan direction perpendicular to the page scan motion of the storage phosphor to form a scanning raster pattern of a matrix of pixels.

There is a problem in the prior art of film/screen radiology in providing multiple images with one exposure. Typically, where a radiologist wishes to see multiple levels of edge enhancement or the same edge enhancement with different tonescales, multiple x-ray exposures had to be taken. This is costly, time consuming and unnecessarily exposes the patient to undesirable x-ray exposure. A further problem is presented when multiple versions of an x-ray image signal are created if a destination for the images can not accept all of the images. For example, due to magnetic storage limitations at a workstation, it may be desirable to route only one version there. A laser printer, on the other hand, can reproduce multiple versions of the same exposure on a single film, so it is desirable to route all the versions to the printer.

SUMMARY OF THE INVENTION

According to the present invention there is provided a solution to this problem in the prior art. In general, the solution comprises producing, from a single x-ray exposure of a patient, multiple versions (images) of the same exposure using different image processing parameters for each version and automatically routing each version to preselected destinations such as a laser printer or a high resolution workstation. According to the present invention an x-ray image processing apparatus comprises:

means for providing an x-ray image signal, having x-ray exam data associated therewith;

image processing means for processing said x-ray image signal for at least one image parameter to produce an image processed x-ray image signal;

database means for storing versions data based on exam type, said versions data including preselected image parameter values for producing different versions of an image processed x-ray image signal, said database means further storing preselected destinations that each version can be sent to; and control means for controlling said image processing means to process said x-ray image signal to create one or more versions of said x-ray image signal as a function of the preselected image parameter values stored in said database for the exam type associated with said x-ray image signal, such that each version has different image parameter values and for routing each version to the preselected destination stored in said database.

Preferably, the means for providing an x-ray image signal includes a storage phosphor reader for converting a latent x-ray image in a storage phosphor into an x-ray image signal.

DESCRIPTION OF THE DRAWINGS

FIGS. 5–16 are screens depicting the functions of a quality control station of the system of FIG. 4.

FIGS. 27 and 28 are views showing image processing default values.

FIG. 30 is a screen depicting a displayed image with a list of destinations.

DESCRIPTION OF THE PREFERRED EMBODIMENTS

Figure 1:
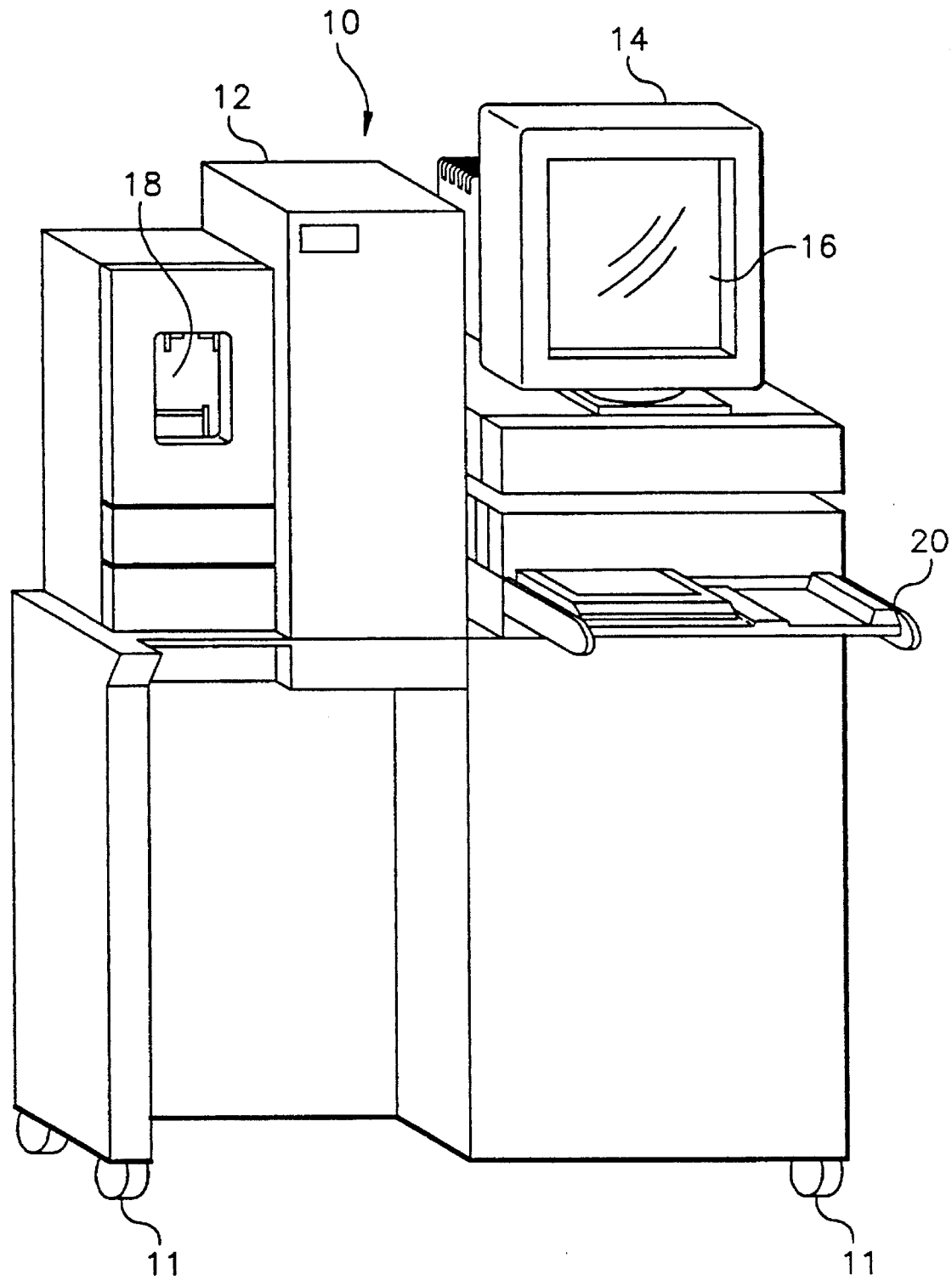
FIG. 1 is a perspective view of a storage phosphor reader.

Referring now to FIG. 1, there is shown a storage phosphor reader 10 incorporating an embodiment of the present invention. Reader 10 is mounted on casters 12 for easy portability in a radiology environment. Reader 10 includes a multiunit housing 12 housing the components of storage phosphor reader 10 and a video monitor 14 having a touch screen 16 supported on housing 12. Housing 12 also includes a bar code reader docking station 18 for docking a hand held bar code reader and for transferring data from the hand held bar code reader to storage phosphor reader 10. Reader 10 includes storage phosphor cassette load platform 20 which receives cassettes containing storage phosphor plates which are to be read or erased by reader 10.

In general, storage phosphor reader 10 processes images captured on a storage phosphor plate using conventional radiographic equipment. Reader 10 then scans the storage phosphor plate and converts the latent x-ray image therein into an electrical x-ray image signal which can be viewed on monitor 14. The scanned image is then delivered to a receiving device (such as a quality control station, laser printer or archival device) for image processing, image enhancement, viewing, printing and/or storage. The storage phosphor reader 10 is operated using touch screen 16 which also displays the image. The storage phosphor plates which are used to hold the unexposed x-ray images are mounted in standard size x-ray cassettes of different sizes. These storage phosphor plates can be erased and reused repeatedly. The optional hand held bar code reader can be used to collect exam information which is transferred to the storage phosphor reader 10 when it is mounted in station 18. The exam information is then associated with the scanned images.

In general, the storage phosphor reader is usable in the storage phosphor patient identification system disclosed in commonly assigned U.S. patent application Ser. No. 963, 036, filed Oct. 19, 1992, inventor Good et al. As disclosed in that patent application, the storage phosphor patient identification system is as follows:

When a radiology technologist receives a request for an x-ray examination of a patient, the technologist exposes a body part of the patient to an x-ray which is stored as a latent x-ray image in the storage phosphor plate of a storage phosphor cassette. Several images may be taken at this time. Using the optional portable bar code reader the technologist scans the patient identification bar code label and the label on the storage phosphor cassette. Exam related information can be scanned from a bar code chart that is usually attached to the portable x-ray generator. Such information includes body part type, x-ray exposure conditions, position of patient and the like.

The image is now captured by the technologist performing the x-ray exam using the cassette containing the storage phosphor plate from which the bar code label was scanned. When the x-ray exam is complete the technologist takes the storage phosphor cassette to storage phosphor reader 10 to be processed. If the optional bar code reader is used, the technologist transfers the patient identification and exam information by inserting the bar code reader into the bar code reader station 18 on the front of reader 10. The scanned information is then transferred to the control system of the storage phosphor reader 10. The technologist then loads the cassette containing the exposed storage phosphor plate into reader 10 by loading on load platform 20. Scanning is initiated when the technologist presses a start button on touch screen 16.

Inside storage phosphor reader 10 the storage phosphor plate is extracted from the cassette and scanned with a laser light. As the plate is scanned, the image appears on touch screen 16 as it is being scanned. After the scanning is complete the image is sent to a receiving device where it can be tonescaled, enhanced, viewed, printed and/or stored. After the storage phosphor plate has been completely scanned it is erased by exposure to light which removes any remnants of the image. The storage phosphor reader 10 then places the storage phosphor plate back into its cassette. The technologist can now remove the cassette from reader 10 to be reused for another exam.

Figure 2:
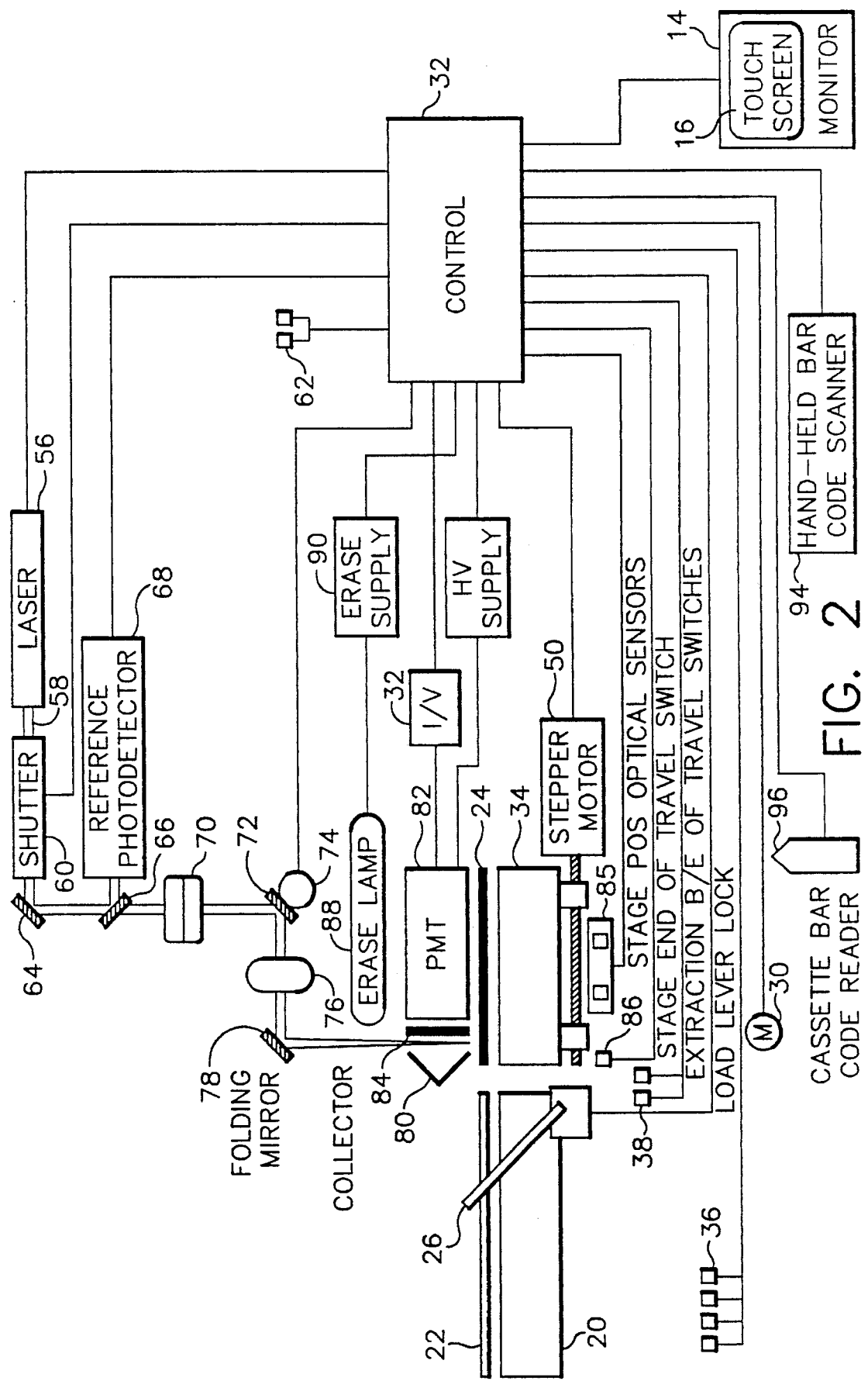
FIGS. 2 and 3 are respectively a partially diagrammatic, partially schematic view and a perspective view of the components of the storage phosphor reader of FIG. 1.
Figure 3:
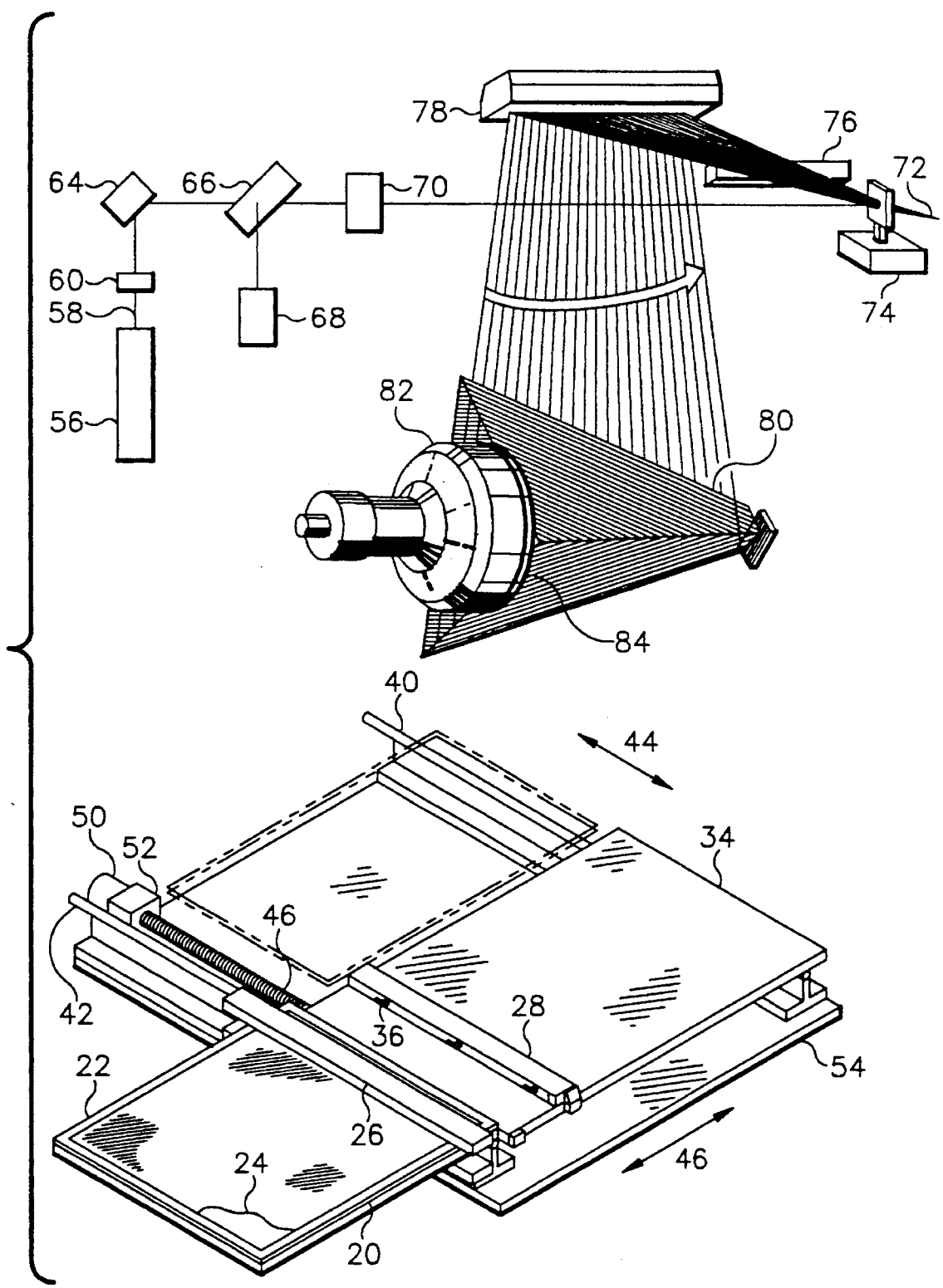

Referring now to FIGS. 2 and 3 there will be described in greater detail a preferred embodiment of storage phosphor reader 10. As shown, a storage phosphor cassette 22 containing a storage phosphor plate 24 is loaded on cassette load platform 20. Load lever 26 is rotated to clamp cassette 22 in place and to latch the cassette 22 to permit extraction of storage phosphor plate 24 therefrom. Storage phosphor plate 24 is extracted from cassette 22 by extraction device 28 (FIG. 3) which is actuated by extraction motor 30 under software control from control 32. Control 32 includes standard computer components such as a microprocessor, a magnetic disk drive for storing images, software applications and computer operating system and input and output devices to communicate with the components of reader 10. Such microcomputer systems are well known in the art and will not be described in detail herein.

Extraction device 28 is slidably mounted on translation stage 34 and includes hooks 36 which engage storage phosphor plate 24. Extraction device 28 extracts storage phosphor plate 24 from cassette 22 onto translation stage 34. As the storage phosphor plate 22 is loaded onto stage 34 it passes over plate size detecting switches 36 which detect the plate size and communicate this information to control 32. There are sufficient plate size detectors 36 to detect the different plate sizes that can be processed by reader 10. The beginning and end of travel of extraction mechanism 28 are sensed by extraction begin and end travel switches 38 connected to control 32.

Translation stage 34 is slidably mounted on rails 40 and 42 for movement in opposite directions 44 which are perpendicular to the directions 46 of loading and unloading of plate 24 relative to translation stage 34. Translation stage 34 is driven by a screw drive mechanism 48 actuated by stepper motor 50 mounted on block 52. Rails 40 and 42 are supported by frame member 54 of reader 10.

The laser scanning components will now be described. Reader 10 includes a laser 56 (such as a helium neon gas laser) for stimulation of storage phosphor plate 24. Laser 56 produces a laser beam 58 which passes through a shutter 60. Shutter 60 is controlled by digital signals received from control 32. Shutter 60 closes with activation of cover interlock switches 62 which detect closure of the housing 12 covers.

Beam 58 is reflected off mirror 64 and passes through beam splitter 66 which directs a portion of the laser beam 58 to reference photodetector 68. Following the beam splitter 66 laser beam 58 passes through collimator 70. The collimated laser beam is deflected by an oscillating scan mirror 72 driven by galvanometer 74 under the control of control 32. Scan mirror 72 provides the line scan raster motion of the laser beam 58. Galvanometer 74 drives mirror 72 with a constant angular velocity.

An f-theta lens 76 produces a flat field of focus and constant linear velocity at the plane of storage phosphor plate 24. Folding mirror 78 directs the laser beam through light collector 80 onto storage phosphor plate 24. Collector 80 may be of the type disclosed in commonly assigned U.S. Pat. No. 5,151,592, issued Sep. 29, 1992, inventors Boutet et al. The stimulating light of laser beam 58 causes the storage phosphor in plate 24 to emit light (blue) which is a function of the x-ray image stored in plate 24. Collector 80 directs this emitted light onto photomultiplier tube (PMT) 82. A filter 84 in front of the face of PMT 82 blocks the scattered stimulating laser light and passes the light emitted by storage phosphor plate 24. Once a storage phosphor plate 24 is on translation stage 34 a scan is begun. Movement of translation stage 34 in the direction of arrow 44 is under software control of control 32. Control 32 sends commands to stepper motor 50 to initiate a scan, to start translation stage 34, to start galvanometer 74 and to turn on PMT 82. From the home position of stage 34 the control 32 counts stepper motor 50 steps to the point where the storage phosphor plate 24 is under collector 80. At this point acquisition of the latent x-ray image on storage phosphor plate 24 begins. At the end of the scan (determined by the number of scan lines for the appropriate storage phosphor plate size), PMT 82 and galvanometer 74 are turned off and translation stage 34 is returned to the home position which is determined by one of the stage position optical sensors 85. A stage end of travel switch 86 is located just beyond the position of optical sensors 84 to prevent damage in case of failure of optical sensors 84.

Immediately after translation stage 34 reaches the home position, erase lamp 88 is turned on by actuation of erase power supply 90 under software control from control 32. Following a predetermined erase time (such as 30 seconds) erase lamp 88 is turned off and extraction mechanism 28 returns storage phosphor plate 24 in the direction of arrow 46 to storage phosphor cassette 22. When the extraction mechanism 28 trips the extraction end of travel switch 38, the lock for load lever 26 is released. The storage phosphor reader user can now rotate load lever 26 and remove cassette 22 from loading platform 20.

During the scan of storage phosphor plate 24 an emitted x-ray light image is converted by PMT 82 into an x-ray electrical current signal. This signal is converted to a voltage by amplifier 92. As described in greater detail in commonly assigned U.S. patent application Ser. No. 965,657, filed Oct. 23, 1992, inventor S. Dhurjaty, entitled "Noise Reduction in a Storage Phosphor Data Acquisition System", laser noise which is present in the x-ray image signal produced by PMT 82 is corrected by subtracting a reference signal detected by reference photodetector 68. The corrected digital signal is corrected for the light collection signature of light collector 80 by a correction lookup table in control 32. The correction lookup table is loaded during calibration of reader 10 when it is initially set up.

Patient identification and examination information are downloaded into reader 10 from a hand held bar code scanner 94 positioned in station 18 of reader 10. As each storage phosphor plate 24 is extracted from its cassette 22 cassette bar code reader 96 reads the bar code on plate 24. The image data and corresponding patient and exam information are correlated by control 32.

The physical size of the cassettes 22 containing the storage phosphor plates 24 are identical to that of conventional radiographic film/screen cassette sizes. Typically storage phosphor reader 10 is capable of reading the following storage phosphor plate sizes: 18×24 centimeters, 24×30 centimeters, 35×35 centimeters, and 35×43 centimeters. The raster pattern or matrix pixel size for each storage phosphor plate that can be processed is, for example, as follows: 18×24 cm −1792×2400; 24×34 cm −2048×2500; 35×35 cm − 2048×2048; and 35×43 cm −2048×2500.

Critical Care System

The storage phosphor reader 10 of FIG. 1 can be part of a critical care system made up of hardware and software that allows radiology technologists to (1) capture images onto a standard cassette which contains a storage phosphor plate using the sites conventional x-ray image capture methods; (2) convert those images into electronic images using the storage phosphor reader 10; (3) using a quality control workstation correct any erroneous patient information, exam information, and, if necessary, the x-ray image look; (4) print the image and its text label on an x-ray laser printer; and (5) enter patient information into the patient database and generate a bar code label for the patient identification. Optionally, the critical care system also allows a requesting physician or radiologist to view the image on a high resolution workstation, such as the Personal Display System supplied by Vortech, of Richardson, Tex. The system can also be expanded to allow optional permanent archiving of x-ray exams on optical disk where it can be retrieved for later viewing or reprinting.

Figure 4:
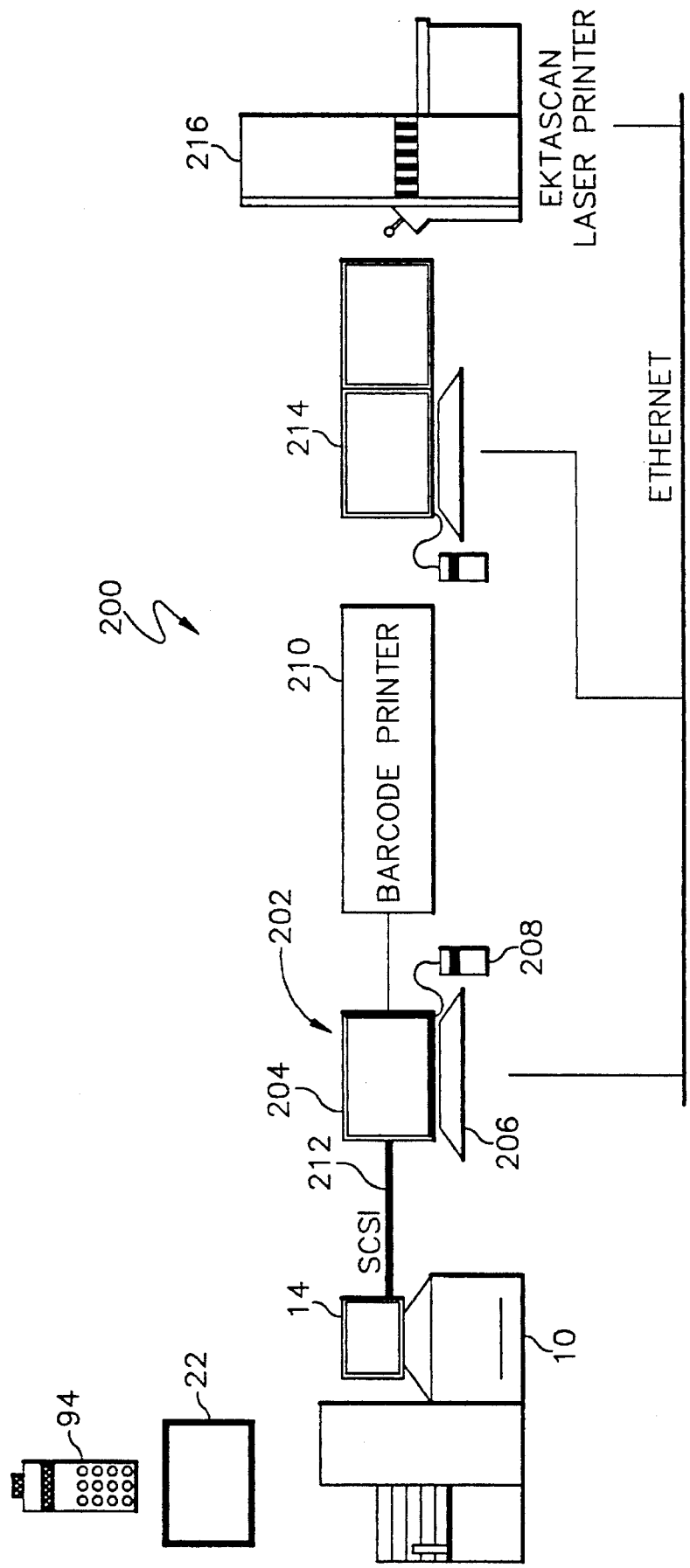
FIG. 4 is a schematic diagram of a critical care system incorporating the present invention.

Referring to FIG. 4, there is shown a diagrammatic view of a critical care system incorporating an embodiment of the present invention. As shown, critical care system 200 includes storage phosphor reader 10 having a control and viewing monitor 14. Reader 10 accepts storage phosphor x-ray cassette 22 for converting an x-ray image in the cassette storage phosphor into a digital x-ray image. A hand-held bar code scanner 94 is provided to download patient ID and exam information into reader 10. System 200 also includes quality control and data entry workstation 202 which includes a high resolution monitor 204, a data entry keyboard 206, and a mouse 208. An optional bar code printer 210 is linked to quality control workstation 202. Storage phosphor reader 10 communicates with work station 202 by means of a communication channel, such as a SCSI communications link 212.

Link 212 passes a raw digital x-ray image from storage phosphor reader 10 to quality control workstation 202. Workstation 202 allows a technologist to view the x-ray image. It also functions as the database server, upon which the demographic database resides. Workstation 202 will be described in greater detail hereinafter, but, in general, provides an interactive data entry interface for the technologist and prints patient ID bar code labels on bar code printer 210. Using the quality control workstation 202, the radiology technologist can modify the image presentation (orientation, tonescale, edge enhancement) and patient or examination information prior to approving the image and routing it to its next destination. The technologist can also modify or add routing information for a patient for a single image.

Quality control workstation 202 can be used in a pass-through mode or a manual mode. In pass-through mode, x-ray exams are processed at the workstation 202 and then routed directly to other destinations, such as high resolution PDS 214, or laser printer 216 (such as a Kodak Ektascan Laser Printer). In manual mode, a user must verify the x-ray image from reader 210 and patient and exam information before releasing it to its destination. The image enhancement which allows for proper display of the images for diagnostic purposes is performed by adaptive unsharp masking processing and tonescaling. The tonescaling algorithms are preferably those described in U.S. patent application Ser. No. 797,615, filed Nov. 25, 1991, inventors Capozzi and Schaetzing, entitled "Method and Apparatus for Automatic Tonescale Generation in Digital Radiographic Images" and U.S. patent application Ser. No. 906,191, filed Jun. 29, 1992, inventors Jang and Schaetzing, entitled "Method for Automatic Foreground and Background Detection in Digital Radiographic Images".

Quality control workstation 202 is linked to high resolution personal display system 214 and laser printer 216 by means of a communication link, such as an Ethernet link. This link may be a hard wire or optical linelink, or a wireless link, or a satellite link.

In general, quality control workstation 202 has sufficient resident memory and fixed disk storage to meet the following requirements: (1) storage of a predetermined number of x-ray exams, (2) patient database, (3) exam information (such as exposure conditions, body part, patient position, etc.), (4) preference information, i.e., image processing parameters for exam types, (5) error and transaction logs, (6) an operating system, (7) application software.

In general, the quality control workstation 202 provides the radiology technologist with the following functions (which will be described in greater detail below with respect to FIGS. 5–16).

1. Check images acquired from storage phosphor reader 10.

2. Correct patient information and x-ray exam information.

3. Adjust image parameters, such as image orientation and window width and level (after they have been automatically enhanced using tonescaling and unsharp masking techniques in workstation 202).

4. Route an acceptable exam or image (automatically or by specification) to one or more destinations such as an x-ray laser printer, a viewing station (PDS) or image archive. In manual mode, the exam must be approved (released) by the technologist before it will be automatically routed to a specified or default destination. Preferably, the image data is transmitted to its destination in a ACR-NEMA (America College of Radiology-National Electrical Manufacturers Association) file which contains the processed image data and ACR-NEMA header (containing patient information and exam information) and applicable lookup tables.

5. Automatically process exams and route them directly to the destinations. This is called pass-through mode.

6. Enter patient information (demographics) into the local (i.e., critical care system) patient database, or access the system patient database.

7. Generate bar code labels for each newly acquired patient identification number and, as necessary, new bar code labels required for the exam data collection card and, optionally, radiology technologist identification.

Figure 5:
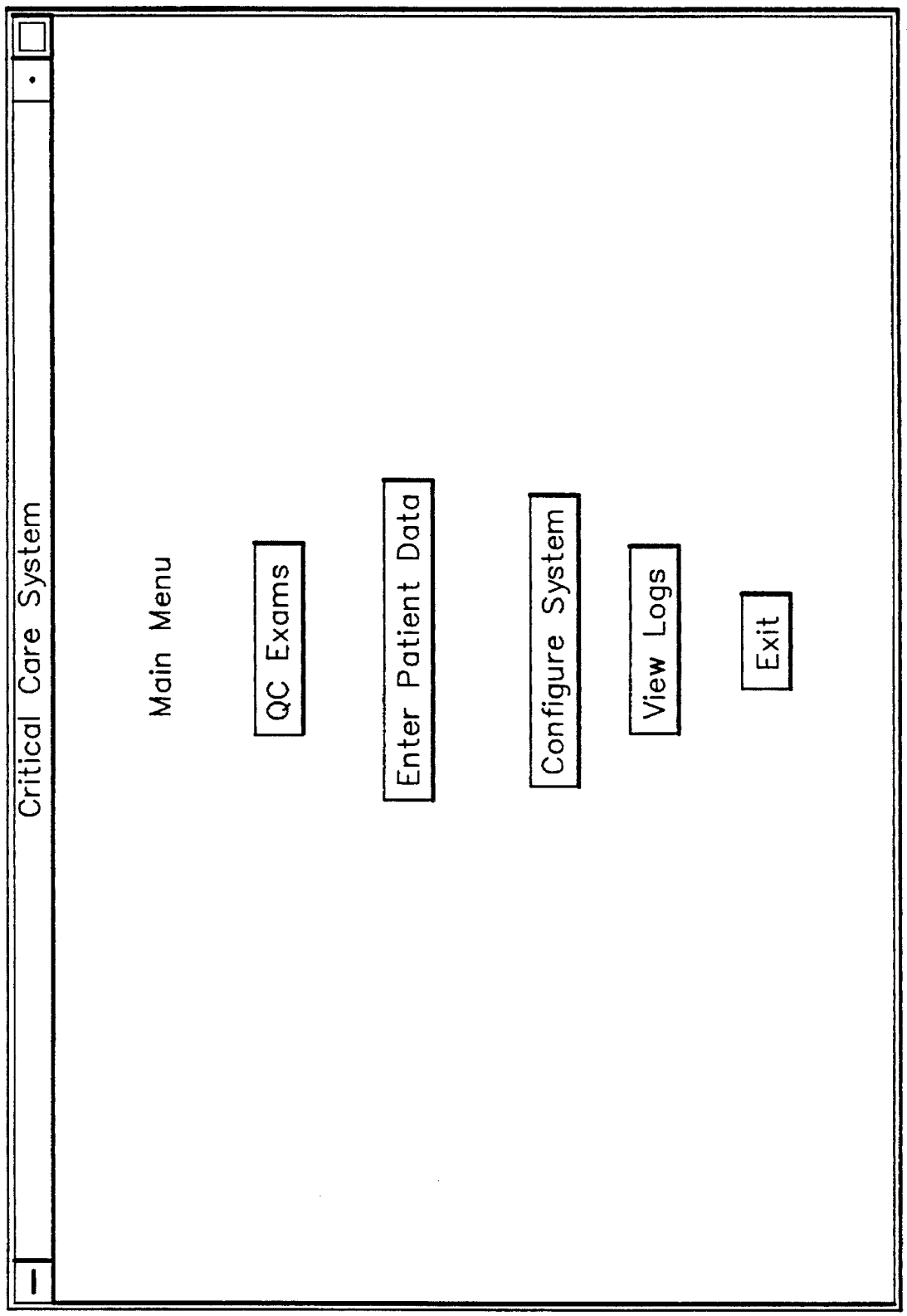

The enumerated functions of quality control workstation 202 will now be described in greater detail with reference to FIGS. 5–16 which depict the screens showing the menus and operations that can be effected by means of a pointer on the screen controlled by a mouse. As shown in FIG. 5, the main menu is used to select the quality control function to be used. Main menu shown in FIG. 5 includes the selectable functions QC exams, enter patient data, configure system, view logs, exit.

Figure 6:
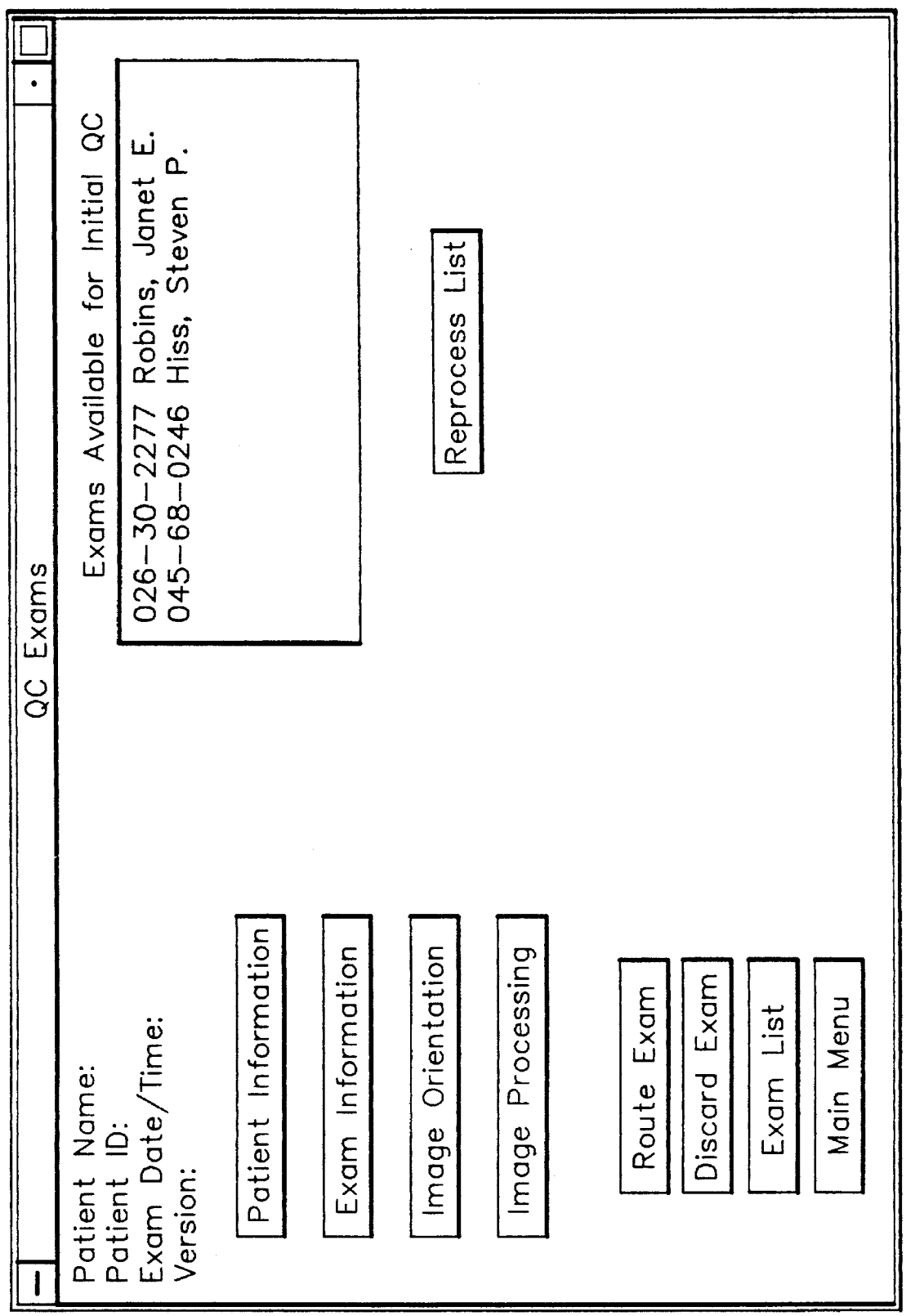

FIG. 6 depicts the QC exams screen with the exams (images) which are available for initial quality control processing. Two exams are listed for ROBBINS and HISS. This screen also indicates several other function buttons which can be selected, i.e., a reprocess list, patient information, exam information, image orientation, image processing, route exam, discard exam, exam list, and main menu. If the reprocess list button is chosen, the screen of FIG. 7 is shown. As shown, exams available for reprocessing include exams of HISS, ROBBINS, and STAHLMAN. The user can select the exam to be viewed from either list.

FIG. 8 shows the QC exam screen with ROUTE EXAM window which appears when the user elects to QC an exam or when the route exam button is selected. The x-ray image will appear in the window on the right hand side of the screen. In the upper left-hand corner of the screen, the patient name, patient ID, exam date/time, and version number are displayed. The route exam window shows exam information to be verified, such as, technologist identification, requisition number, cassette identification, x-ray exam projection, body part, position, distance, exposure kilovoltage (k VP), exposure milliamps (mAs), exposure index, and comment. In the lower left-hand region, the select exam destinations window indicates the four destinations that the exam display can be routed, i.e., ICU 1 PDS, ICU 2 PDS, radiology KELP (laser printer), archive. In the lower left-hand corner, the route exam and modify exam buttons may be selected.

Figure 9:
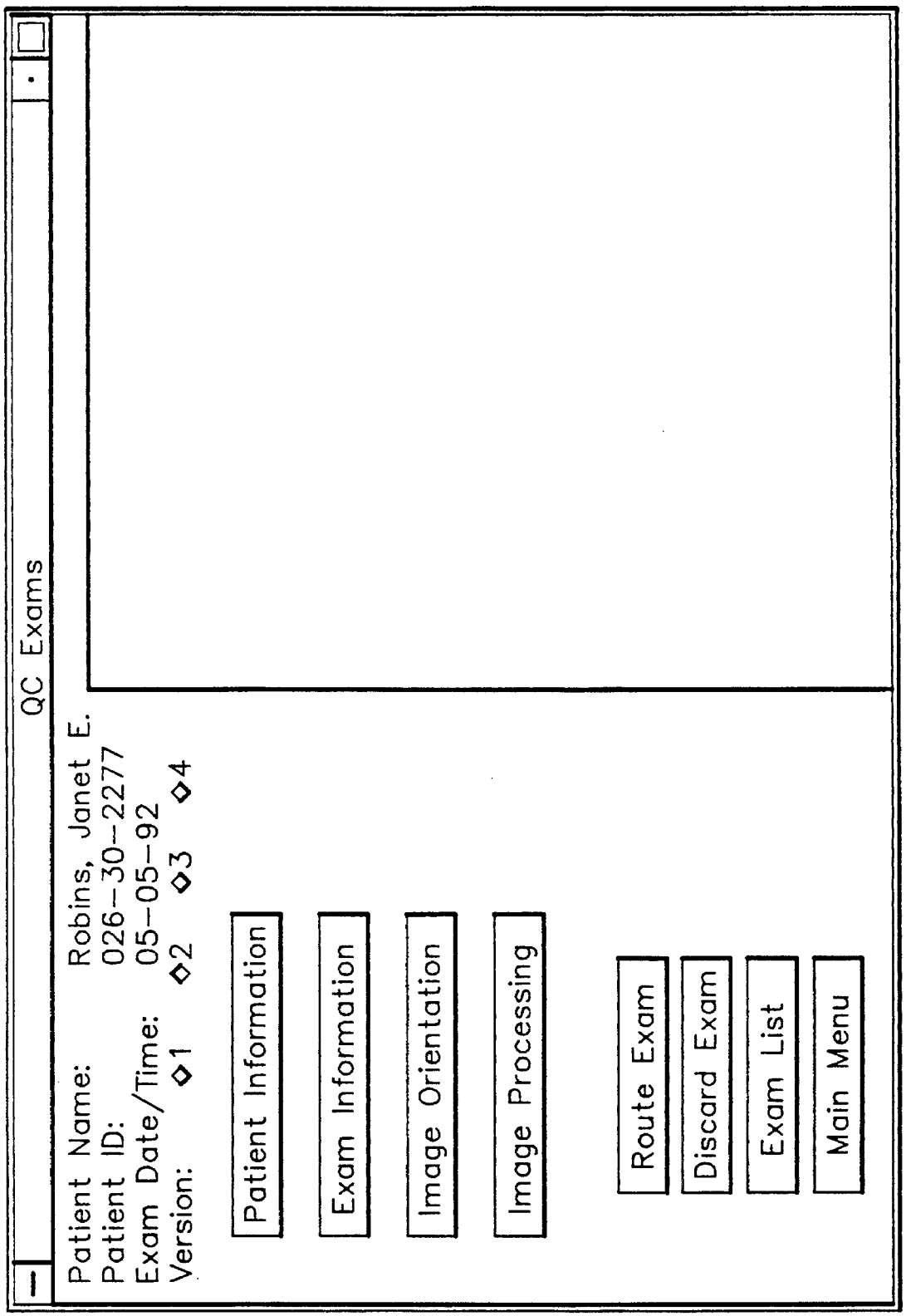
Figure 10:
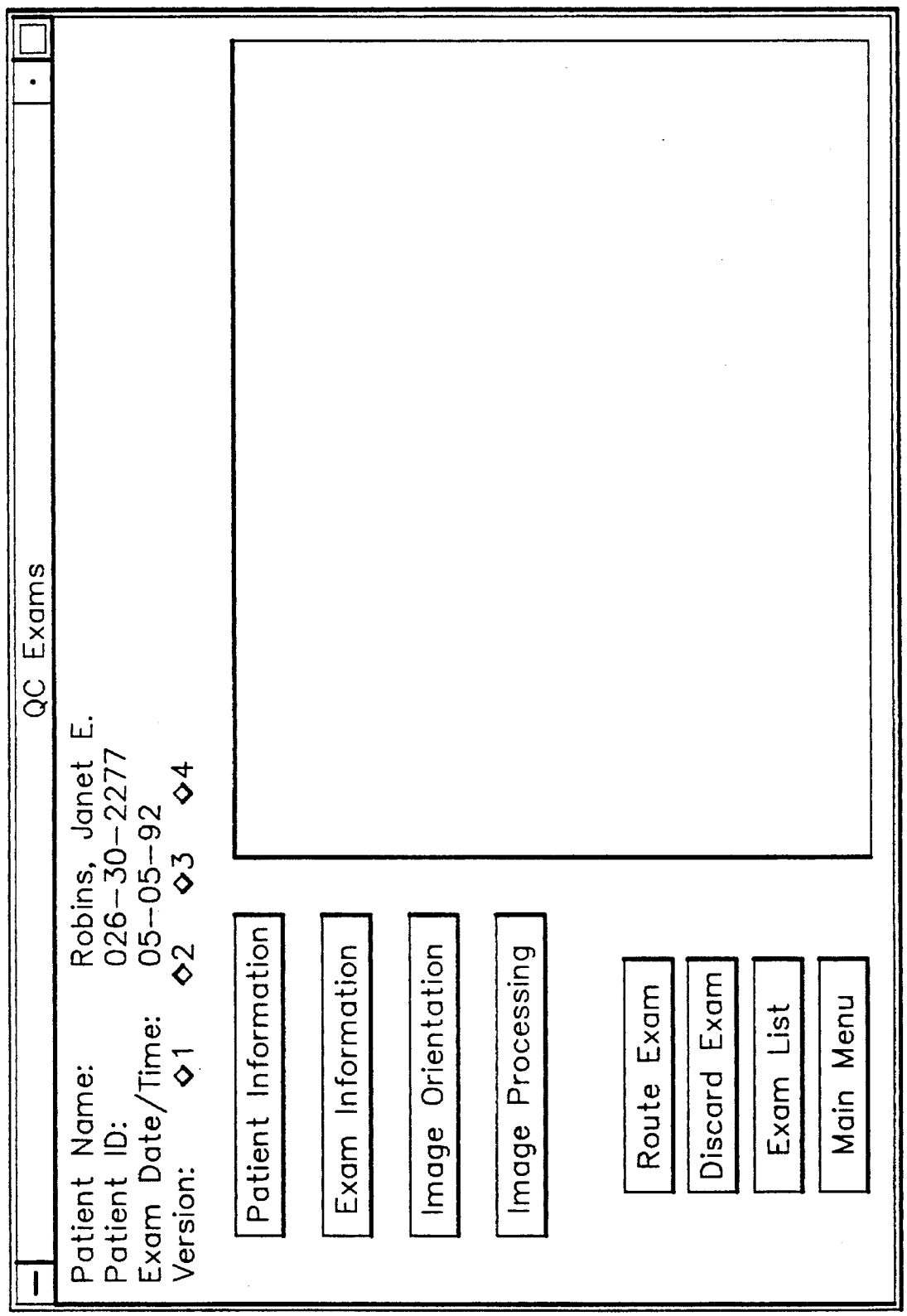

Referring to FIGS. 9 and 10, there are respectively shown the QC exam screen with portrait image display and landscape image display. The function buttons on the left-hand side allow the selection of any of the functions for the currently displayed image.

Referring to FIG. 11, the screen shown is the QC exam screen with patient information window. The patient information window is displayed when the patient information button, shown in FIG. 10, is selected. The patient information window shows the following patient information, i.e., patient name, patient ID, date of birth, patient sex, radiologist, referring physician, room/unit number, bed number, hospital, department, diagnosis, and destinations. The process buttons in the lower left-hand corner are update, reset and done. The operator of QC workstation can enter, verify or change the patient information with this screen displayed.

Referring to FIG. 12, the QC exam screen with exam information window is shown. The exam information window is displayed when the exam information button is selected. In the exam information window shown on the left-hand side of the screen, the following exam information are listed: technologist ID, requisition number, cassette ID, projection, body part, position, distance, KVP, MAS, exposure index, and comments. Any of these exam information items can be changed by the user. Again, the lower left-hand corner depicts the update, reset and done buttons for selection.

Figure 13:
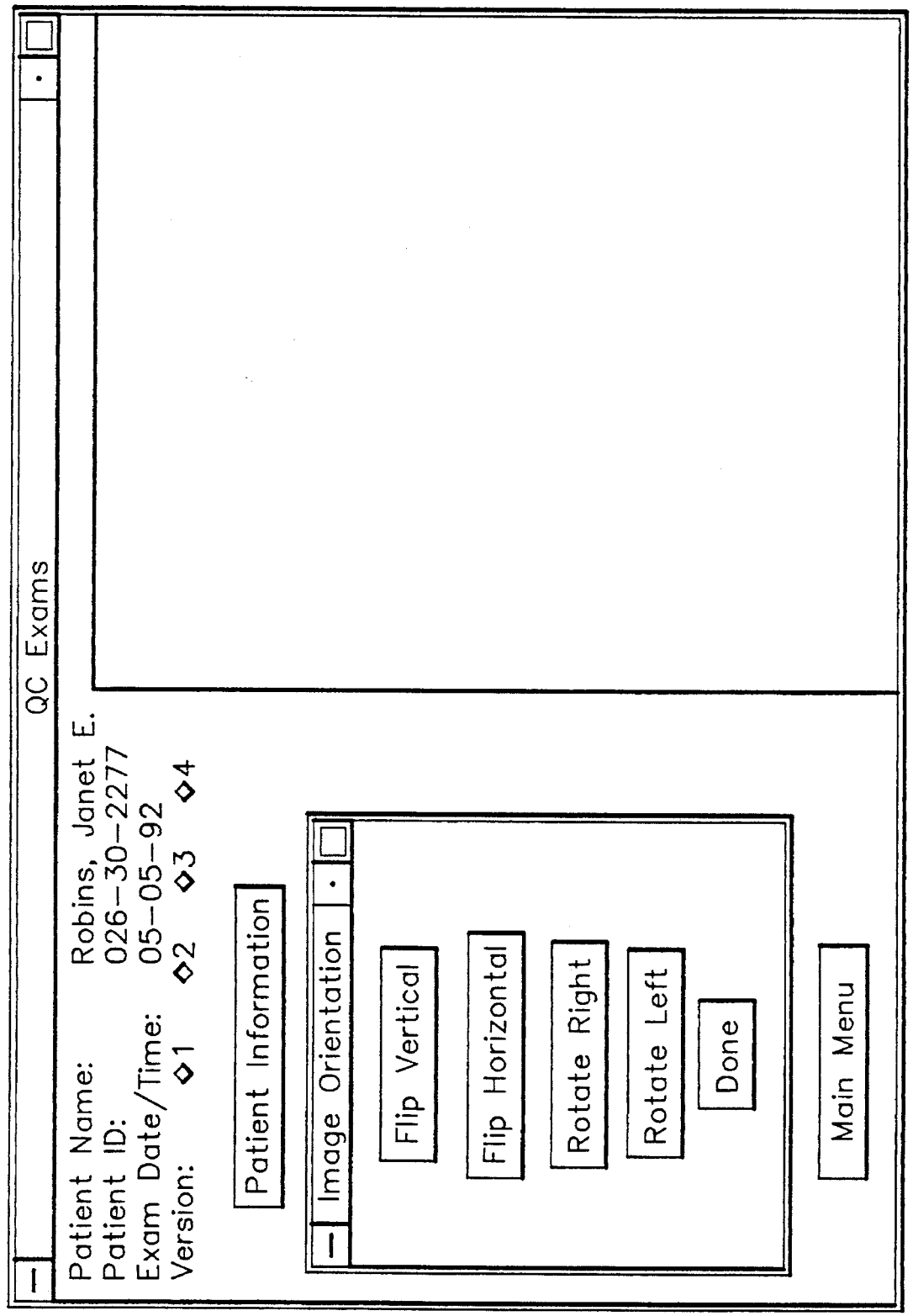

Referring to FIG. 13, the screen shows the QC exam screen with orientation window. This window is displayed when the image orientation button is selected. As shown in the image orientation window on the left-hand side, the buttons which are selectable are FLIP VERTICAL which effects flipping the image 180° about the horizontal axis; FLIP HORIZONTAL which effects flipping the image 180° about the vertical axis; ROTATE RIGHT which effects rotating the image 90° clockwise from the vertical axis; and ROTATE LEFT which effects rotation of the displayed image 90° counterclockwise from the vertical axis.

If necessary, the image and its versions are automatically orientated (rotated left) upon arrival at the quality control station 202 from storage phosphor reader 10. This orientation is based on the storage phosphor plate 24 orientation as read in storage phosphor reader 10 and described in greater detail above. When the image is displayed, the user can select to reorient it. All versions are also rotated automatically. In addition, depending on the print format of the laser printer 216, the images may have to be automatically rotated in order to be printed on film. For example, a "portrait" mode image can be sent to a printer as if it is to be printed "1-up" on a 14×17 film. If it is to be printed as "2-up", both images must be rotated before they are sent.

Figure 14:
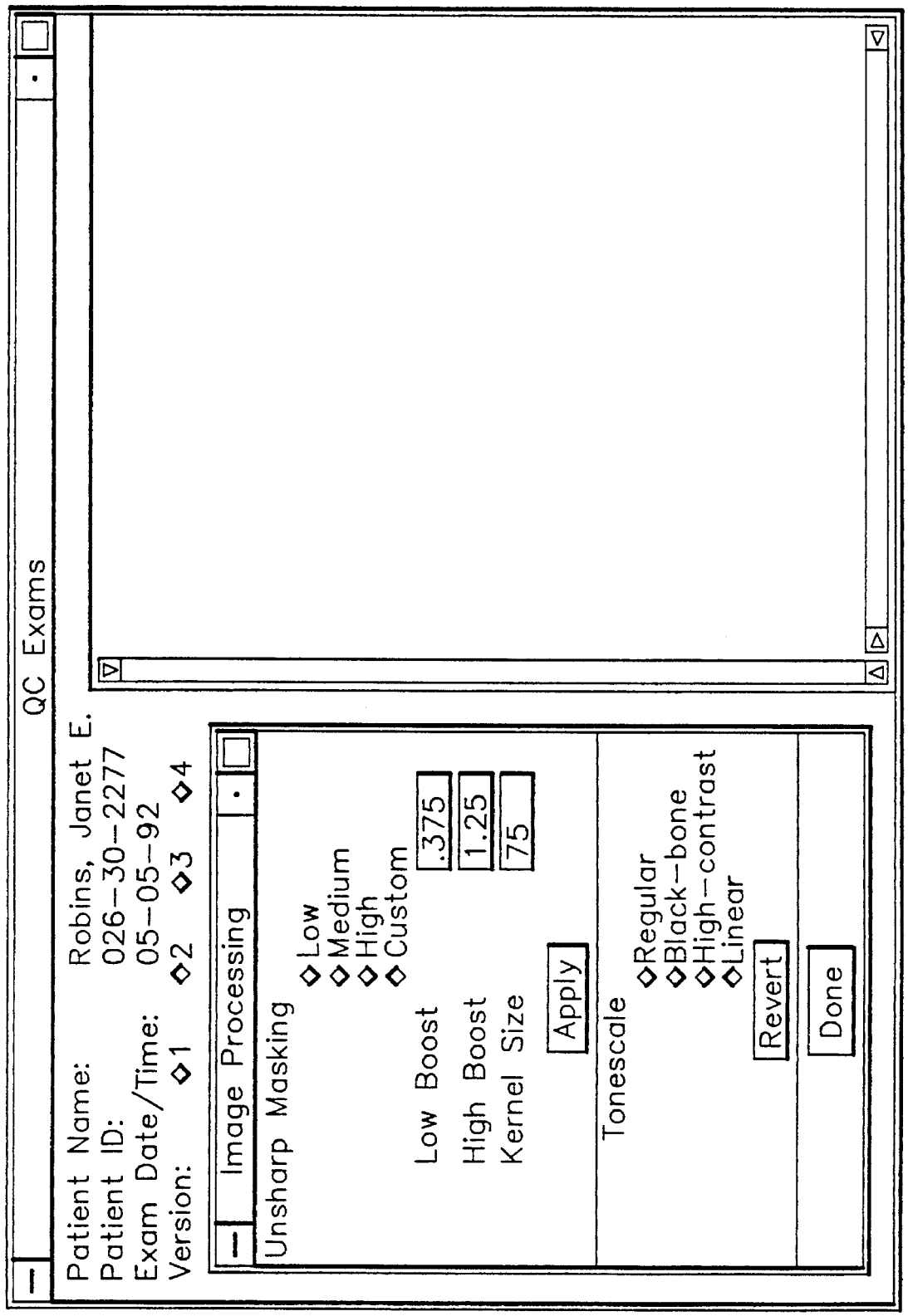
Figure 15:
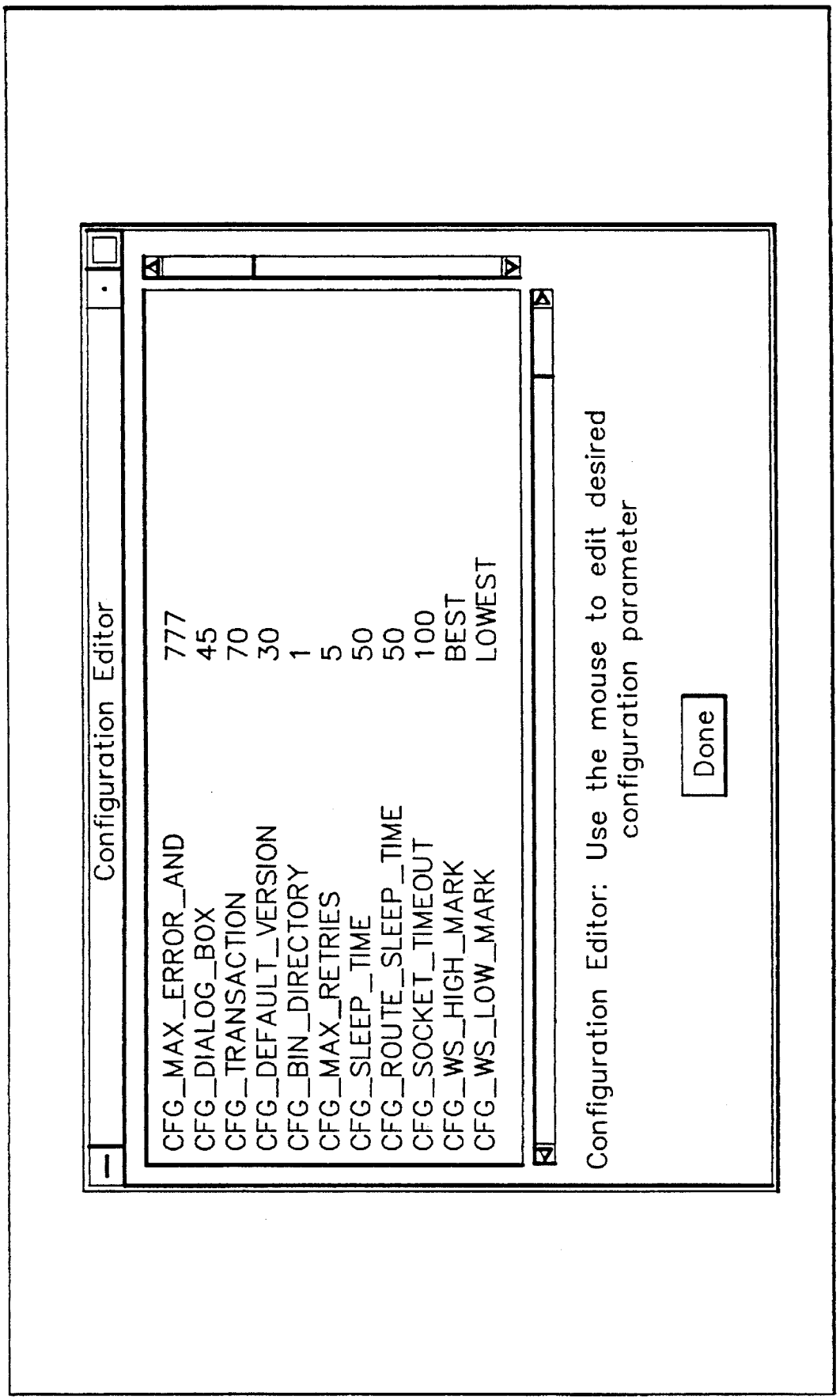
Figure 16:
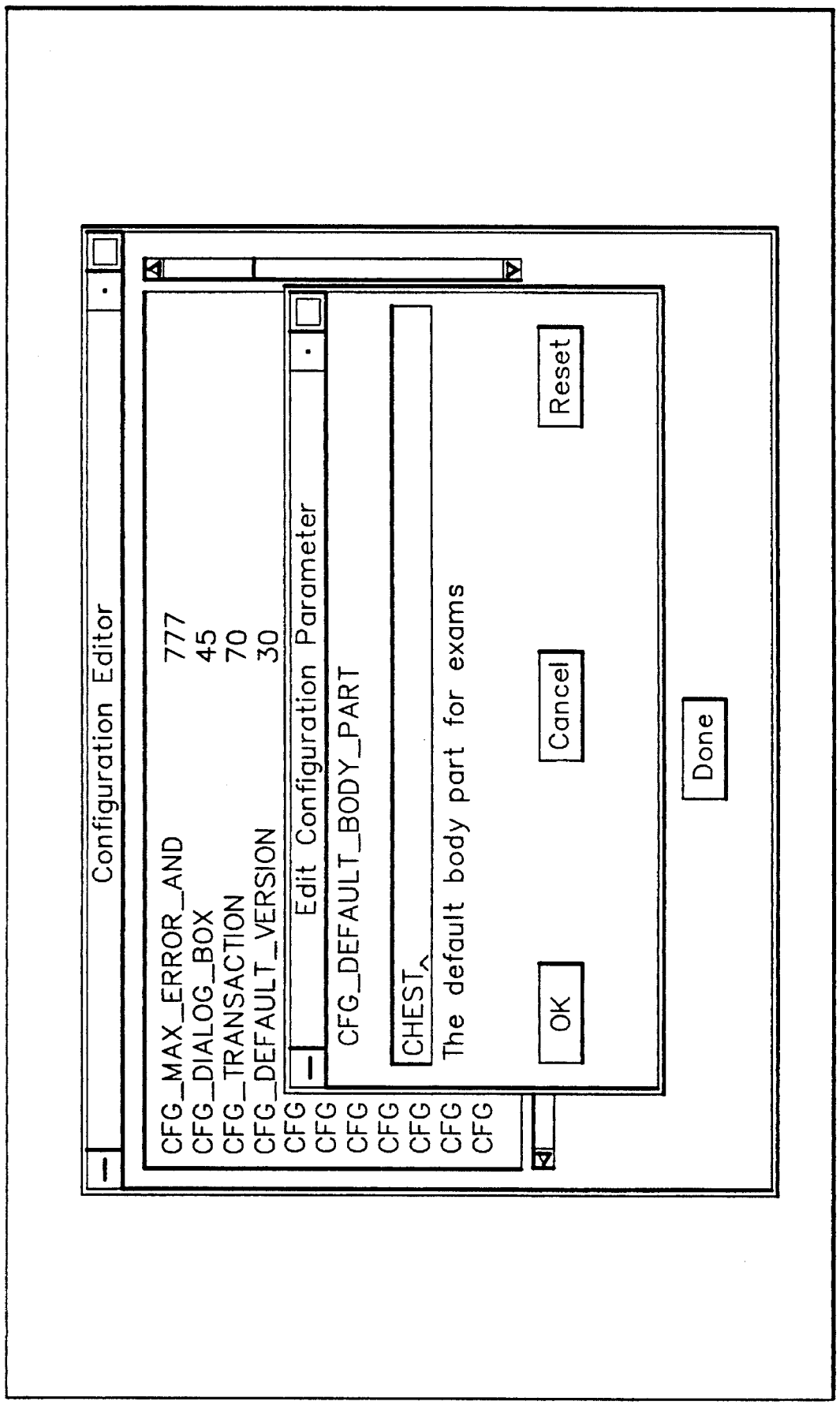

Referring to FIGS. 14, 15, and 16, they will be briefly described before more detailed explanation of the functions shown thereon. FIG. 14 shows the QC exam screen with image processing window, which allows the user to change image processing parameters for the currently displayed version. This window appears when an exam is selected for reprocessing, or when the image processing button is selected. FIG. 15 shows the configuration screen where a user selects a configuration parameter to change. FIG. 16 shows a configuration edit screen where a user enters the value for the configuration parameter using this screen.

Figure 17:
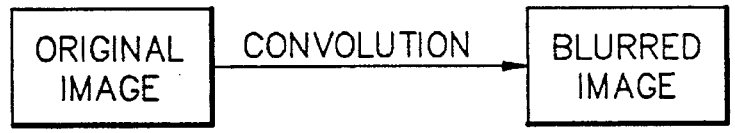
FIGS. 17–20 are diagrammatic views useful in illustrating unsharp masking image processing.
Figure 18:

Referring again to FIG. 14, the image processing functions will be described in greater detail. As shown in the image processing window on the left, image processing parameters include unsharp masking parameters and tonescale parameters. In general, unsharp masking, or edge enhancement, is applied to an image to produce an image with lines or edges that are more clearly defined. This is done by first "blurring" a copy of the image through convolution. Convolution is a mathematical process which multiplies the image by a kernel. The size of the kernel determines the number of weight factors and, therefore, the extent to which the image is blurred. This is depicted in FIG. 17. The blurred image is then subtracted from the original image to create an "edges only" image. This is depicted in FIG. 18. High and low boost factors are applied selectively to the "edges only" image and added back into the original image which produces the unsharp mask image.

Figure 19:
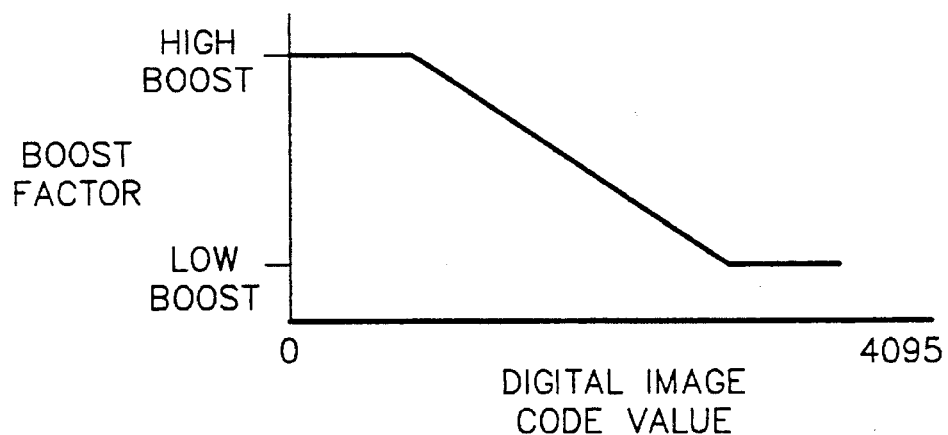

A histogram of the image is first derived as depicted in FIG. 19, which is a graphical representation of boost versus digital image value. The high boost is applied on the low intensity part of the image (left part of histogram) and the low boost on the high intensity part. There is a linear transition between the high and low boost values which is determined by the "threshold value and width" parameters that are created by an auto tonescaling algorithm.

Figure 20:
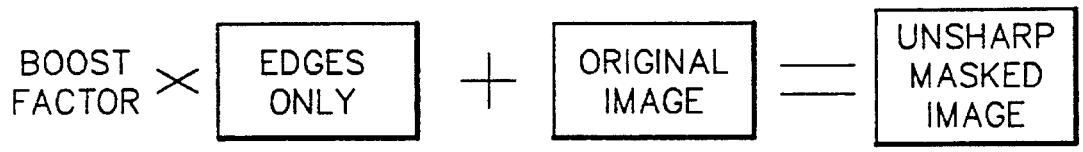
Figure 21:
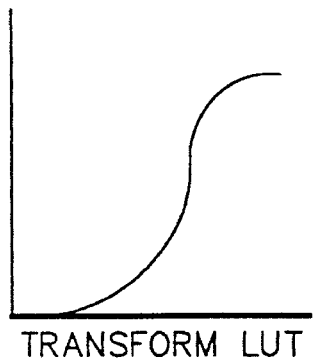
FIGS. 21–24 are graphical views useful in illustrating tonescale image processing.

The unsharp masking algorithm preferably used by the image processing software of workstation 202 is as follows: P prime (new pixel) = P (current pixel) + B (boost factor) × (P $-\bar{p}$ (kernel average)). Changing low or high boost factors impacts the presentation of the edges in the low and high intensity part of the image. This is depicted in FIG. 20.

The preferences for unsharp masking (kernel size and boost factors) can be specified according to body part. If the body part or the values are changed specifically, then the unsharp masking process must be performed again (kernel size is the region of pixels surrounding the pixel being processed. For example, a kernel size of 75 would encompass a matrix of 75×75 pixels with the processed pixel being at the center of the matrix).

Referring again to FIG. 14, in the image processing window a user can select low, medium, high or custom unsharp masking, low boost, high boost, and kernel size. As shown, for custom unsharp masking the low boost factor is selected as 0.375, the high boost factor is selected as 1.25, and the kernel size is selected as 75 (75×75 matrix).

The tonescale selections available to a user are indicated under the tonescale heading as regular, black-bone, high contrast, or linear. These tonescale look-up tables are applicable to the version selected to be displayed on the display area of the screen of FIG. 14. When raw image data is received by quality control workstation 202 from storage phosphor reader 10, a tonescale transformation look-up table is generated according to the computed radiography image processing algorithms disclosed in the above referenced U.S. patent application Ser. Nos. 797,615 and 906,191. The transform look-up table (LUT) provides the optimal mapping of the raw image data to film using exam type, histogram, etc., information. The transform LUT can be modified at workstation 202 by the user, if the original LUT failed to produce an optimal image look. A typical graphical representation of a tonescale transform as derived above is shown in FIG. 19.

Figure 22:
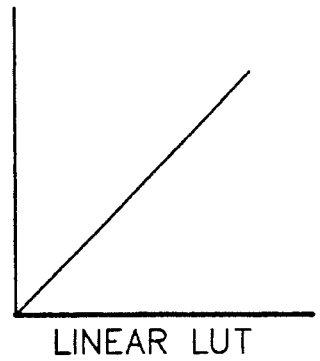

The tonescale buttons shown in the image processing window of FIG. 14 allow the user to perform the following tonescaling operations on the transform LUT:

1. Replace the transform LUT by a linear LUT as shown in FIG. 22.

Figure 23:
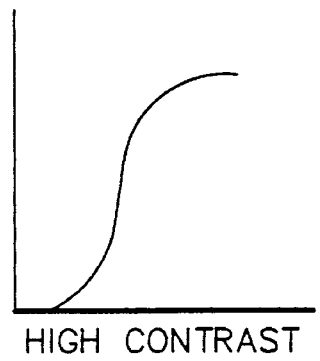

2. Replace the transform LUT by a high contrast LUT, as shown in FIG. 23.

Figure 24:
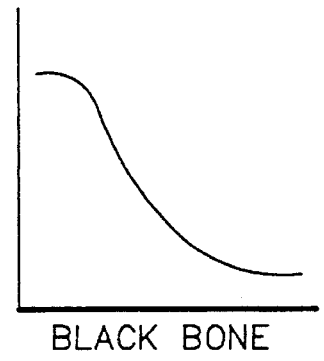

3. Replace the transform LUT by a black-bone LUT as shown in FIG. 24.

Figure 25:
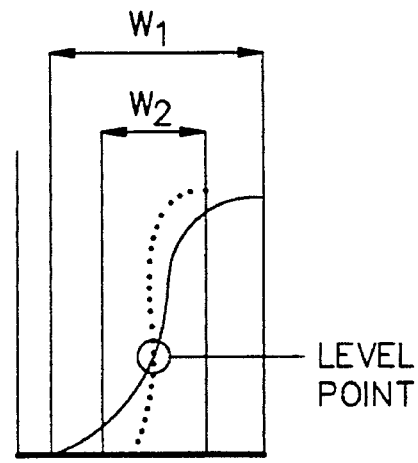
FIGS. 25–26 are diagrammatic views useful in illustrating window width and level image processing.
Figure 26:
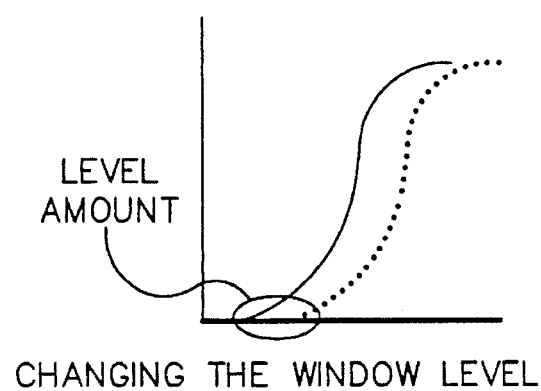

4. Change window width or/and window level. Window width and level changes are actually multiplications and additions to the transform LUT. These changes (also called deltas) are stored in the image (version) header so that the user can determine what changes have been made to the original LUT based on these values and parameters. FIGS. 25 and 26 illustrate the effect of changing window width and window level on a transform LUT. FIG. 14 is provided with vertical and horizontal scroll bars which allow changing of window width by moving up and down the vertical scroll bar and allow changing window level by moving left and right on the horizontal scroll bar.

5. Revert to the original LUT based on exam type by selecting the revert button.

6. Change the exam type so that the LUT for that exam type is applied.

Any change to a look-up table is applied only to the currently selected version.

The image processing parameter defaults are set for each exam type and maximum number of versions. FIG. 27 shows illustrative unsharp masking default values, and FIG. 28 shows illustrative tonescale default values.

Version Requirements

QCW 202 produces multiple versions of a single digital x-ray image signal from storage phosphor reader 10. (It will be understood that the digital x-ray image signal can be produced by other digital x-ray image sources, such as diagnostic imaging modalities, film digitizers.) For each raw image, the quality control workstation 202 generates at least one enhanced version. The number of versions generated is determined by the Exam Type (Body Part and Projection). If there is no Exam Type for the raw image, then the default number of versions is used as specified by the Super Tech/Applications Specialist or System Administrator.

The following parameters must be specified for each version:

type of Look Up Table (LUT) to apply (standard, high contrast, or blackbone);

boost parameters and kernel size (used for unsharp masking);

which version is viewable during initial QC (During initial QC, only one version will be displayed. During reprocessing, the user can look at any of the versions).

During initial processing, one of the versions is enhanced (i.e., tonescaled and unsharp masked) and made available (if in manual mode) for viewing and modifications. If the QCW 202 is operating in pass-through mode, each version is enhanced before it is sent to its destination(s).

In manual mode:

the user can select an individual version. (The raw data file is not available before the exam is initially QC'd.)

The user can change any of the following image processing parameters only for the currently selected version:

tonescale type;

window/level (change tonescaling interactively);

unsharp masking type;

low boost factor;

high boost factor;

kernel size.

In order to change the tonescaling or unsharp masking for other versions, the user must select the version and then specify the changes. If the user chooses to revert to the original tonescaling, the tonescaling only for the currently selected version is changed (i.e., revert is not available for unsharp masking parameters nor can tonescale changes be applied globally to all versions). If the user elects to reorient the currently displayed image, all versions are also rotated and/or flipped. If the user changes the Exam Type, the image processing parameters are changed for all versions.

Destination types can be specified for each version for each Exam Type. If sent to a laser printer, one, two or four versions can be printed so that up to four versions can be designated to be routed to the printer. Of these destination types, only one version can be designated (as specified by the Super Tech/Application Specialist) to be sent to a Personal Display Station (PDS) destination type. If the exam is routed to more than one PDS, each PDS will receive the same version.

The QCW 202 contains, as part of its internal software, a relational database. In this database there is data for each patient, such as patient name, patient ID number, patient sex, bed number, radiologist, etc. There is also data for each examination, such as patient ID number (which is used to match patient data), body part, examination projection, milliampere-seconds, kilovolts, exposure distance, technician ID number, etc.

There is yet another database table that is associated with version of examination images, based on body part and projection combinations. Body parts in the system are CHEST, SKULL, ABDOMEN, EXTREMITY, TSPINE, CSPINE, CLAVICLE, etc. Projections are AP, PA, LLD, RLD, etc. For each body part and projection combination, there is an entry in the "version table" that relates it with the number of versions to create for an examination of that type, which version shall be displayed to the technologist before diagnosis, and, for each version, the image processing parameters to perform on the examination data for that version.

For instance, there would be a database entry for AP CHEST examinations. It may list a desire for four versions to be created, the first of which is the one to be shown to the technologist during quality control (QC). All four versions are edge enhanced using low boost and high boost values of 0.75 and 1.25 respectively. The first two versions have a kernel size of 51, while the last two versions use 75 as the kernel size. Versions one and three both use a regular tonescale look up table (LUT), version two uses a high-contrast LUT, and version four uses a blackbone LUT. When an AP Chest examination is performed, the examination data (distance, body part, etc.) is transferred from the KESPR along with the examination image data. The database is queried for version information based on body part and projection (CHEST & AP), and the QCW software prepares the appropriate versions (four in this case). Once the technologist views the appropriate version (first one) and routes the examination to a laser printer, all versions are printed for diagnosis.

Default Values

When Quality Control Workstation 292 is installed by a service person, it is set up with certain defaults for the image processing parameters. These defaults are set up in the Configuration File as shown in FIGS. 15 and 16.

The following values must be specified in the Configuration File:

default Body Part (variable name: CFG_DEFAULT_BODY_PART);

default Projection (variable name: CFG_DEFAULT_PROJECTION);

default Radiologist (variable name: CFG_DEFAULT_RADIOLOGIST);

Kernel Size values for High, Medium, and Low (variable names: CFG_HIGH_KERNEL_SIZE, CFG_MEDIUM_KERNEL_SIZE, and CFG_LOW_KERNEL_SIZE);

High Boost values for High, Medium, and Low (variable names: CFG_HIGH_HIGH_BOOST, CFG_MEDIUM_HIGH_BOOST, and CFG_LOW_HIGH_BOOST);

Low Boost values for High, Medium, and Low (variable names: CFG_HIGH_LOW_BOOST, CFG_MEDIUM_LOW_BOOST, and CFG_LOW_LOW_BOOST.

In addition, there can be Kernel Size, High Boost Factor, and Low Boost Factor values for a specific Body Part, such as:

High, Medium, and Low values for Kernel Size for Chests (variable names: CFG_CHEST_HIGH_KERNEL_SIZE, CFG_CHEST_MEDIUM_KERNEL_SIZE, and CFG_CHEST_LOW_KERNEL_SIZE);

High, Medium, and Low values for High Boost for Chests (variable names: CFG_CHEST_HIGH_HIGH_BOOST, CFG_CHEST_MEDIUM_HIGH_BOOST, and CFG_CHEST_LOW_HIGH_BOOST);

High, Medium, and Low values for Low Boost for Chests (variable names: CFG_CHEST_HIGH_LOW_BOOST, CFG_CHEST_MEDIUM_LOW_BOOST, and CFG_CHEST_LOW_LOW_BOOST).

Preferences

There can be specified the values that a radiology site uses most frequently in the Preferences. Values for preferences are set up according to:

Radiologist;
Body Part;
Projection; and
Version.

That is, there are values for each Radiologist/Body Part/Projection/Version unique combination that you want to specify.

There can be specified the following values for each unique combination:

Unsharp Masking Boost Factor (High, Medium, Low, or Custom);

High Boost Factor (used only if the Unsharp Masking Boost Factor is Custom);

Low Boost Factor (used only if the Unsharp Masking Boot Factor is Custom);

Kernel Size (used only if the Unsharp Masking Boost Factor is Custom);

Tonescale Type (Regular, Blackbone, High Contrast, or Linear);

Average Density;
LUT Start Out;
Viewable Version;
Destination Type: Printer;
Destination Type: Display (Personal Display System);
Destination Type: Archive.

Determining Which values to Use

When an exam is received by the QCW 202 from storage phosphor reader 10, the Preferences are searched to determine if there is a match for the exam's Radiologist/Body Part/Projection.

Note: A match against the Preferences can be made at any time during the following process. When a match is made, the process continues as described later in When the Values are Found.

If Radiologist preferences are not implemented in QCW 202 software, a match is usually not found. In this case, the Default Radiologist (CFG_DEFAULT_RADIOLOGIST) is extracted from the Configuration File.

The Preferences are then searched using the Default Radiologist, the exam's Body Part and Projection.

If no match for Default Radiologist and exam's Body Part and Projection then find Default Body Part and Default Projection. The Preferences are then searched using the Default Radiologist, Default Body Part, and Default Projection.

A match must be found when the Preferences are searched for a match using the Default Radiologist, Default Body Part, and Default Projection.

Note: The Radiologist, Body Part, and Projection are not actually changed in the Patient or Exam Information when the defaults are used. The defaults are temporarily assigned to the exam only for the purpose of determining the correct values to use for image processing.

When the Values are Found

When a match is found in the Preferences, the number of versions to be produced and, if the QCW 202 is in Manual QC Mode, the version number of the Viewable Version, are extracted.

The raw image is then rotated if necessary (based on the Plate Orientation contained in the Exam Information).

Then the Unsharp Masking Boost Factor is examined for the Viewable Version (if in Manual QC Mode) or the first version (if in Pass-Through mode). If the value of the Unsharp Boost Factor is Custom, then the values for High Boost Factor, Low Boost Factor, and Kernel Size are used to edge-enhance the image. If the value of the Unsharp Boost Factor is High, Medium, or Low, then the values for High Boost, Low Boost, and Kernel Size are extracted from the Configuration File. If the Body Part is Chest (or has been defaulted to Chest), then the specific values for Chest are used (that is, Chest High Boost, Chest Low Boost, and Chest Kernel Size). If the Body Part is anything other than Chest, then the generalized defaults are used (i.e., High Boost, Low Boost, and Kernel Size). Unsharp masking is then performed on the version using the appropriate High Boost, Low Boost, and Kernel Size values. The version is then tonescaled according to the Tonescale Type for the version.

In Manual QC Mode, the Viewable Version is displayed. In Pass-Through Mode, the next version is enhanced. (In Manual QC Mode, additional versions are enhanced when the user selects a different version to view or routes the exam.)

Case Studies

This section contains examples of how the values for image processing are determined.

Assume the Configuration File is set up as follows:
Assume the Configuration File is set up as follows:

TABLE 1

Configuration File

| Variable Description | Variable Name | Value |
|---|---|---|
| Default Body Part | CFG_DEFAULT_BODY_PART | Chest |
| Default Projection | CFG_DEFAULT_PROJECTION | AP |
| Default Radiologist | CFG_DEFAULT_RADIOLOGIST | Dr. Default |
| Kernel size value for HIGH | CFG_HIGH_KERNEL_SIZE | 37 |
| Kernel size value for MEDIUM | CFG_MEDIUM_KERNEL_SIZE | 37 |
| Kernel size value for LOW | CFG_LOW_KERNEL_SIZE | 37 |
| High Boost size value for HIGH | CFG_HIGH_HIGH_BOOST | 1.5 |
| High Boost size value for MEDIUM | CFG_MEDIUM_HIGH_BOOST | 1.0 |
| High Boost size value for LOW | CFG_LOW_HIGH_BOOST | 0.5 |
| Low Boost size value for HIGH | CFG_HIGH_LOW_BOOST | 1.5 |
| Low Boost size value for MEDIUM | CFG_MEDIUM_LOW_BOOST | 1.0 |
| Low Boost size value for LOW | CFG_LOW_LOW_BOOST | 0.5 |
| For Body Part of CHEST, Kernel size value for HIGH | CFG_CHEST_HIGH_KERNEL_SIZE | 75 |

TABLE 2

Configuration File

| Variable Description | Variable Name | Value |
|---|---|---|
| For Body Part of CHEST, Kernel size value for MEDIUM | CFG_CHEST_MEDIUM_KERNEL_SIZE | 75 |
| For Body Part of CHEST, Kernel size value for LOW | CFG_CHEST_LOW_KERNEL_SIZE | 75 |
| For Body Part of CHEST, High Boost size value for HIGH | CFG_CHEST_HIGH_HIGH_BOOST | 1.5 |
| For Body Part of CHEST, High Boost size value for MEDIUM | CFG_CHEST_MEDIUM_HIGH_BOOST | 1.0 |
| For Body Part of CHEST, High Boost size value for LOW | CFG_CHEST_LOW_HIGH_BOOST | 0.5 |
| For Body Part of CHEST, Low Boost size value for HIGH | CFG_CHEST_HIGH_LOW_BOOST | 0.5 |
| For Body Part of CHEST, Low Boost size value for MEDIUM | CFG_CHEST_MEDIUM_LOW_BOOST | 0.25 |
| For Body Part of CHEST, Low Boost size value for LOW | CFG_CHEST_LOW_LOW_BOOST | 0.125 |

Assume the Preferences File is set up as follows:

TABLE 3

| Radiologist | Body Part | Projection | Ver. # | Preferences Viewable Vers. | USM Boost Fctr. | High Bst. | Low Bst. | Kernel Size | Tone-scale Type |
|---|---|---|---|---|---|---|---|---|---|
| Dr. Default | Chest | AP | 1 | 2 | High | 0 | 0 | 0 | Reg. |
| Dr. Default | Chest | AP | 2 | 2 | Med. | 0 | 0 | 0 | Reg. |
| Dr. Default | Cheat | AP | 3 | 2 | High | 0 | 0 | 0 | High Cntrst |
| Dr. Default | Chest | AP | 4 | 2 | Med. | 0 | 0 | 0 | Linear |
| Dr. Default | Abdomen | Lateral | 1 | 1 | Low | 0 | 0 | 0 | Linear |
| Dr. Default | Abdomen | Lateral | 2 | 1 | Med. | 0 | 0 | 0 | Linear |
| Dr. Default | Abdomen | Lateral | 3 | 1 | Med. | 0 | 0 | 0 | Blackbone |
| Dr. Default | Abdomen | Lateral | 4 | 1 | Cust. | 2.0 | 1.5 | 55 | Linear |
| Dr. Jones | Chest | Lateral | 1 | 1 | High | 0 | 0 | 0 | Reg. |
| Dr. Jones | Chest | Lateral | 2 | 1 | Cust. | 3 | 1.2 | 45 | Reg. |
| Dr. Default | Skull | AP | 1 | 1 | Med. | 0 | 0 | 0 | Reg. |

Note: There are usually more fields in the Preferences than are shown above. These fields will need to be updated when adding or making changes to the Preferences, but they are omitted here for clarity.

Assume the following Destination Types are also set up in the Preferences File:

TABLE 4

| | Destination Types (Preferences) | | | | | |
|---|---|---|---|---|---|---|
| Radiologist | Body Part | Projection | Ver. # | ? Printer | ? Display | ? Archive |
| Dr. Default | Chest | AP | 1 | Y | N | N |
| Dr. Default | Chest | AP | 2 | Y | Y | N |
| Dr. Default | Chest | AP | 3 | Y | N | N |
| Dr. Default | Chest | AP | 4 | Y | N | N |
| Dr. Default | Abdomen | Lateral | 1 | Y | Y | N |
| Dr. Default | Abdomen | Lateral | 2 | Y | N | N |
| Dr. Default | Abdomen | Lateral | 3 | Y | N | N |
| Dr. Default | Abdomen | Lateral | 4 | Y | N | N |
| Dr. Jones | Chest | Lateral | 1 | Y | N | N |
| Dr. Jones | Chest | Lateral | 2 | Y | N | N |
| Dr. Default | Skull | AP | 1 | Y | Y | N |

Case Study 1

While in Manual QC Mode, the QCW 202 receives an exam that includes the following Exam Information:

TABLE 5

| Exam Information for Case Study 1 | |
|---|---|
| Field | Value |
| Body Part | Chest |
| Projection | AP |
| Radiologist | Dr. Anthony |

1. The QCW 202 checks the Preferences looking for a match to Dr. Anthony (Radiologist), Chest (Body Part), and AP (Projection).

2. No match is found. The Default Radiologist (as specified in the Configuration File) is substituted for the Radiologist and the check is performed again using the following values:

TABLE 6

| Field | Value |
|---|---|
| Body Part | Chest |
| Projection | AP |
| Radiologist | Dr. Default |

3. A match is found. The following information is extracted from the Preferences File:

TABLE 7

| Preferences for Dr. Default/Chest/AP | | | | | |
|---|---|---|---|---|---|
| Ver. # | Viewable Version | USM Boost Factor | High Boost | Low Boost | Kernel Size | Tone-scale Type |
| 1 | 2 | High | 0 | 0 | 0 | Reg. |
| 2 | 2 | Med. | 0 | 0 | 0 | Reg. |
| 3 | 2 | High | 0 | 0 | 0 | High Contrast |
| 4 | 2 | Med. | 0 | 0 | 0 | Linear |

4. Because the QCW 202 is operating in Manual QC Mode, version 2 is enhanced first.

5. The Configuration File (FIG. 15) is checked for the values to be used for "Medium" edge enhancement:

TABLE 8

| Configuration File | | |
|---|---|---|
| Variable Description | Variable Name | Value |
| For Body Part of CHEST, Kernel size value for MEDIUM | CFG_CHEST_MEDIUM_KERNEL_SIZE | 75 |
| For Body Part of CHEST, High Boost size value for MEDIUM | CFG_CHEST_MEDIUM_HIGH_BOOST | 1.0 |
| For Body Part of CHEST, Low Boost size value for MEDIUM | CFG_CHEST_MEDIUM_LOW_BOOST | 0.25 |

6. Version 2 is enhanced using the following values:

TABLE 9

| Parameter | Value |
| --- | --- |
| High Boost | 1.0 |
| Low Boost | 0.25 |
| Kernel Size | 75 |
| Tonescale Type | Regular | and displayed on the screen.

Case Study 2

While in Pass-Through Mode, the QCW 202 receives an exam that includes the following Exam Information:

TABLE 10

| Exam Information for Case Study 2 | |
| --- | --- |
| Field | Value |
| Body Part | Chest |
| Projection | RLD |
| Radiologist | Dr. Anthony |

1. The QCW 202 checks the Preferences File looking for a match to Dr. Anthony (Radiologist), Chest (Body Part), and RLD (Projection).

2. No match is found. The Default Radiologist (as specified in the Configuration File) is substituted for the Radiologist and the check is performed again using the following values:

TABLE 11

| Field | Value |
| --- | --- |
| Body Part | Chest |
| Projection | RLD |
| Radiologist | Dr. Default |

3. No match is found. The Default Body Part and Default Projection (as specified in the Configuration File) is substituted for the Body Part and Projection (respectively) and the check is performed again using the following values:

TABLE 12

| Field | Value |
| --- | --- |
| Body Part | Chest |
| Projection | AP |
| Radiologist | Dr. Default |

4. The following information is extracted from the Preferences File:

TABLE 13

| Preferences for Dr. Default/Chest/AP | | | | | |
| --- | --- | --- | --- | --- | --- |
| Ver.# | Viewable Version | USM Boost Factor | High Boost | Low Boost | Kernel Size | Tonescale Type |
| 1 | 2 | High | 0 | 0 | 0 | Reg. |
| 2 | 2 | Med. | 0 | 0 | 0 | Reg. |
| 3 | 2 | High | 0 | 0 | 0 | High Contrast |
| 4 | 2 | Med. | 0 | 0 | 0 | Linear |

5. Because the QCW 202 is operating in Pass-Through Mode, version 1 is enhanced first.

6. The Configuration File is checked for the values to be used for "High" Boost Factors to enhance Version 1:

TABLE 14

| Configuration File | | |
| --- | --- | --- |
| Variable Description | Variable Name | Value |
| For Body Part of CHEST, Kernel size value for HIGH | CFG_CHEST_HIGH_ KERNEL_SIZE | 75 |
| For Body Part of CHEST, High Boost size value for HIGH | CFG_CHEST_HIGH_ HIGH_BOOST | 1.5 |
| For Body Part of CHEST, Low Boost size value for HIGH | CFG_CHEST_HIGH_ LOW_BOOST | 0.5 |

7. Version 1 is enhanced using the following values:

TABLE 15

| Parameter | Value |
| --- | --- |
| High Boost | 1.5 |
| Low Boost | 0.5 |
| Kernel Size | 75 |
| Tonescale Type | Regular |

8. The Configuration File is then checked for the values to be used for "Medium" Boost Factors to enhance Version 2:

TABLE 16

| Configuration File | | |
| --- | --- | --- |
| Variable Description | Variable Name | Value |
| For Body Part of CHEST, Kernel size value for MEDIUM | CFG_CHEST_MEDIUM_ KERNEL_SIZE | 75 |
| For Body Part of CHEST, High Boost size value for MEDIUM | CFG_CHEST_MEDIUM_ HIGH_BOOST | 1.0 |
| For Body Part of CHEST, Low Boost size value for MEDIUM | CFG_CHEST_MEDIUM_ LOW_BOOST | 0.25 |

9. Version 2 is enhanced using the following values:

TABLE 17

| Parameter | Value |
| --- | --- |
| High Boost | 1.0 |
| Low Boost | 0.25 |
| Kernel Size | 75 |
| Tonescale Type | Regular |

10. The Configuration File is then checked for the values to be used for "High" Boost Factors to enhance Version 3:

TABLE 18

| Configuration File | | |
| --- | --- | --- |
| Variable Description | Variable Name | Value |
| For Body Part of CHEST, Kernel size value for HIGH | CFG_CHEST_HIGH_ KERNEL_SIZE | 75 |
| For Body Part of CHEST, High Boost size value for HIGH | CFG_CHEST_HIGH_ HIGH_BOOST | 1.5 |

TABLE 18-continued

Configuration File

| Variable Description | Variable Name | Value |
|---|---|---|
| For Body Part of CHEST, Low Boost size value for HIGH | CFG_CHEST_HIGH_LOW_BOOST | 0.5 |

11. Version 3 is enhanced using the following values:

TABLE 19

| Parameter | Value |
|---|---|
| High Boost | 1.5 |
| Low Boost | 0.5 |
| Kernel Size | 75 |
| Tonescale Type | High Contrast |

12. The Configuration File is then checked for the values to be used for "Medium" Boost Factors to enhance Version 4:

TABLE 20

Configuration File

| Variable Description | Variable Name | Value |
|---|---|---|
| For Body Part of CHEST, Kernel size value for MEDIUM | CFG_CHEST_MEDIUM_KERNEL_SIZE | 75 |
| For Body Part of CHEST, High Boost size value for MEDIUM | CFG_CHEST_MEDIUM_HIGH_BOOST | 1.0 |
| For Body Part of CHEST, Low Boost size value for MEDIUM | CFG_CHEST_MEDIUM_LOW_BOOST | 0.25 |

13. Version 4 is enhanced using the following values:

TABLE 21

| Parameter | Value |
|---|---|
| High Boost | 1.0 |
| Low Boost | 0.25 |
| Kernel Size | 75 |
| Tonescale Type | Linear |

14. After all 4 versions are processed, they are automatically routed to their destinations according to their Destination Types and the Destinations specified in the Patient Database (FIG. 11).

TABLE 22

| Version # | Printer? | Display? | Archive? |
|---|---|---|---|
| 1 | Y | N | N |
| 2 | Y | Y | N |
| 3 | Y | N | N |
| 4 | Y | N | N |

Case Study 3

While in Manual QC Mode, the QCW 202 receives an exam that includes the following Exam Information:

TABLE 23

Exam Information for Case Study 3

| Field | Value |
|---|---|
| Body Part | Abdomen |
| Projection | AP |
| Radiologist | Dr. Default |

1. The QCW checks the Preferences looking for a match to Dr. Default (Radiologist), Abdomen (Body Part), and AP (Projection).

2. No match is found. The Default Radiologist (as specified in the Configuration File) is substituted for the Radiologist and the check is performed again using the following values:

TABLE 24

| Field | Value |
|---|---|
| Body Part | Abdomen |
| Projection | AP |
| Radiologist | Dr. Default |

3. No match is found. The Default Body Part and Default Projection (as specified in the Configuration File) is substituted for the Body Part and Projection (respectively) and the check is performed again using the following values:

TABLE 25

| Field | Value |
|---|---|
| Body Part | Chest |
| Projection | AP |
| Radiologist | Dr. Default |

4. A match is found and processing proceeds the same as for Case Study 1. Notice that the values for Chest are used even though the ones for Abdomen Lateral may actually be closer to those preferred.

Destinations

Unlike what is available with screened film, multiple images (versions) may be created from one exposure. Since the exam is digital once read by storage phosphor reader 10, the exam may be digitally routed to multiple printer 216 or workstation 214 destinations, based on rules or simply chosen by the technologist at the QCW 202. Which versions get routed to which network destinations depends on the body part and on the destination type.

Once the technologist views the appropriate version (first one) and approves the examination for diagnosis, it is routed to the appropriate network destination(s).

What exactly the 'appropriate' destination is depends on a hierarchy of rules. If the patient database table contains any default destination(s), then the examination is automatically routed there. If there are no destinations specified in the patient database table, then the examination is automatically routed to the destination(s) that corresponds to the body part. The QCW 202 software is configured to have default destinations for each body part. Lastly, the QCW 202 graphical user interface allows the technologist to override these preferences and choose any routing destination that is configured to be on the network. An examination may be routed to multiple destinations simultaneously.

The versions database table has, in addition to the image processing parameters for each version, an entry that specifies which destination types this examination may be sent to. Therefore, for an AP CHEST examination, as in the example, the four versions will be constructed, however only version three would be sent to a PDS workstation 214 and all four versions would be sent to laser printer 216 as a four-up (for instance).

Routing to Destination(s)

When the user determines that the image appearance is acceptable, the Patient and Exam Information is correct and the desired destinations are selected, the user "OK's" the exam. The exam is routed to its destination(s) or its versions are sent to their independently-specified destinations.

This is carried out by a hierarchy of rules:

Should the destinations be specified for the Patient through the User Interface the exam will be routed there. (The destinations shown will be valid destinations on the network.)

Figure 29:
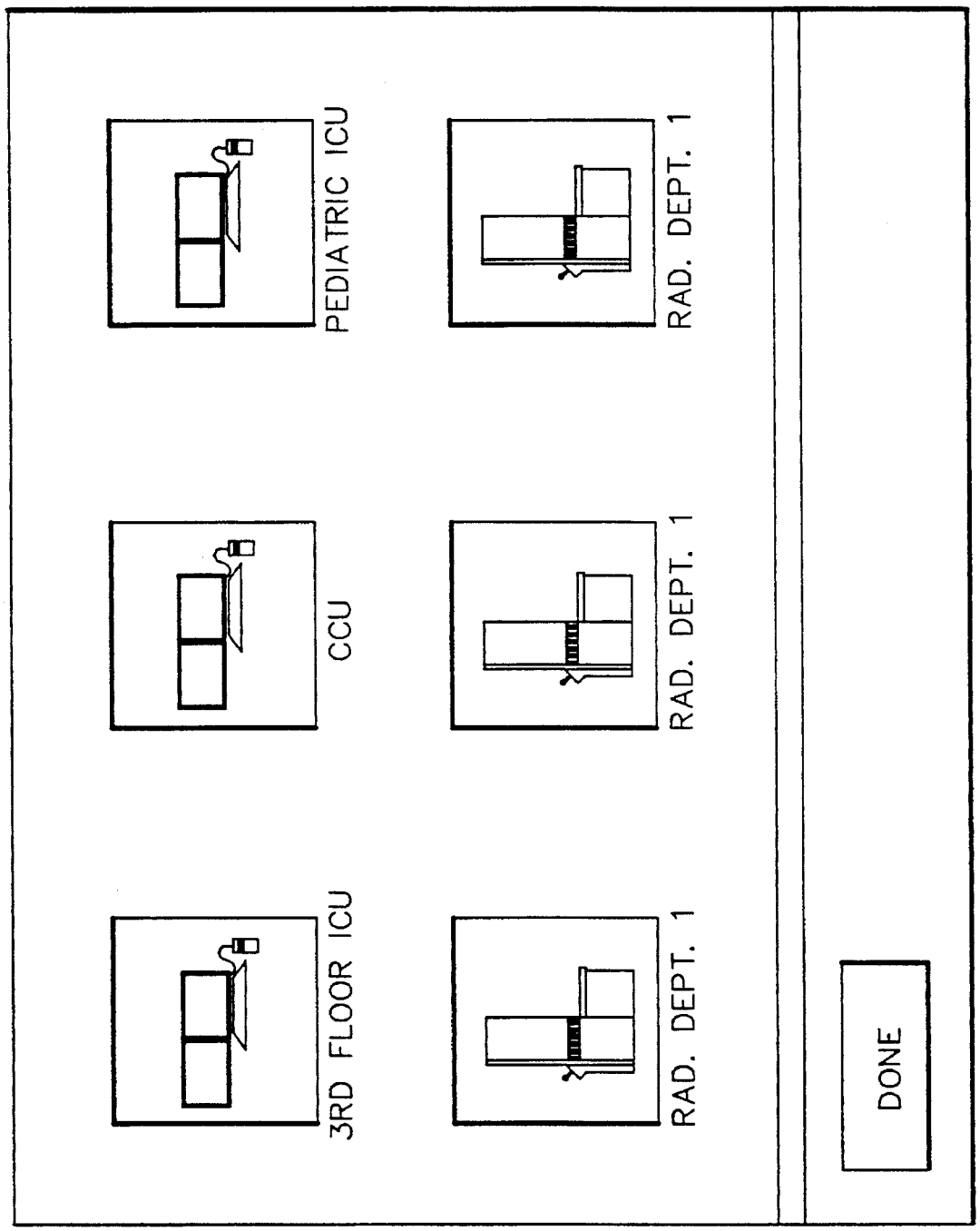
FIG. 29 is a graphical view of destination icons.

Referring to FIG. 29, to specify a destination, one clicks on the icon of the destination of where the patient's exams should be sent. You can select more than one destination. Selected icons are highlighted. To "de-select" a destination click on the highlighted icon. If there are no destinations specified during Patient Demographic data entry (FIG. 11) or if there are none in the patient database for a particular patient, the exam will be routed to a default destination. The QCW 202 software will accomplish this by "looking" into a destinations file that will contain default destinations (valid destinations which will be on the network) based on body part and present them to the user in a list box (shown below).

The list of destinations (FIG. 30, FIG. 8) shows all destinations that the exams can be sent to. The destinations that are highlighted are those that were selected when Patient Demographic data was entered. If none were specified, then the selected destinations are the defaults for the exam's body part.

To select a destination, click on it so that it is highlighted.

To de-select a destination, click on it so that it is no longer highlighted.

Click on "Route Exam" to send the exam to the destination(s) chosen.

When destination(s) are selected from the default list (based on the exam's body part) they are saved in the destinations table inside the exams database so that when this exam is viewed at some later time we know what destination(s) the exam was routed to. When viewing the exam at some later time, it is these destinations that will appear in the list box. In the exams database, the destinations table contains a unique identification number (an exam_id_key) for the exam as well as the destination(s) to route it to.

The destination table has this form:

TABLE 26

| exam id key | Destination |
| --- | --- |
| 1 | KELP-Rad. Dept. 1 |
| 1 | KELP-Rad. Dept. 2 |
| 2 | PDS-CCU |

This table reads as: Route this exam (exam_id key 1) to the printer 216 in Radiology Department 1 and to the printer 216 in Radiology Department 2 and so forth.

TABLE 27

| VERSION | DESTINATION TYPE |
| --- | --- |
| 1 | Printer |
| 2 | Printer, PDS |
| 3 | Printer |
| 4 | Printer |

Assume that these following destinations are selected.
KELP 1
KELP 2
PDS 1
The exam will be Routed as follows:

| VERSION NO. | DESTINATION TYPE | DESTINATIONS |
| --- | --- | --- |
| 1 | Printer | KELP 1 and KELP 2 |
| 2 | Printer, PDS | KELP 1, KELP 2, and PDS 1 |
| 3 | Printer | KELP 1 and KELP 2 |
| 4 | Printer | KELP 1 and KELP 2 |

The number of prints can be changed to the quantity of printed films that are wanted. In addition, exams are formatted according to the number of versions. For example, if an exam has four versions, it will be printed as a 4-up. An exam with one version is printed as a 1-up. Specifying the number of prints does not change the number of "ups" created. If the film is to be printed as soon as possible, the selection box for the Print Priority is used to indicate that the exam should be printed "STAT". The exam will then be printed before any other awaiting printing.

Advantages

The advantage of the routing features of the Critical Care System is that it allows for multiple destinations with various versions going to each. This permits multiple radiologists to take part in the diagnosis. Using screened film, radiologists currently may only have multiple 'destinations' utilized by exposing two pieces of screened film simultaneously.

Another advantage to these routing features is that the system allows for multiple versions to all be printed at a printer, while routing only one version to a high resolution workstation. Personal Display Stations are diagnostic workstations that have the same magnetic storage limitations that all computers have. To route all versions to routing destinations regardless of destination type would potentially misuse computer space.

Lastly, these routing features enable hospitals to configure a radiological image network by placing diagnostic displays in Radiology and in the ICUs, while utilizing existing laser printers that need not be located conveniently for diagnosis.

If so configured, versions of examinations may be routed to those locations based on radiologists' preferences.

Although the invention has been described with reference to preferred embodiments thereof it will be understood that variations and modifications can be effected within the spirit and scope of the invention as described above and as defined in the appended claims.

What is claimed is:

1. A method of processing and routing an x-ray image signal comprising the steps of:

providing an x-ray image signal having one or more of the following data associated with said signal, data identifying a radiologist, data denoting a body part, data denoting an x-ray projection;

providing a first data base having data for a default radiologist, a default body part, and a default x-ray projection;

providing a second data base having preference data for radiologists, body parts, x-ray projections, and a body part/x-ray projection combination, for each body part/x-ray projection combination—a number of versions of the provided x-ray image signal to be produced, including edge enhancement image processing parameters and tonescale image processing parameters for each version, and one or more destinations for each said version;

searching said second data base to determine if there is a match for the radiologist data associated with said provided x-ray image signal, and if no match is found, searching said first data base for the default data of said default radiologist and associating said default radiologist data with said provided x-ray image signal;

searching said second data base to determine if there is a match for the default radiologist and body part and x-ray projection data associated with said provided x-ray image signal, and if no match is found, searching said first data base for the data of said default radiologist and default body part and default x-ray projection, and temporarily associating said default body part and default x-ray projection with said provided x-ray image signal;

searching said second data base to determine that there is a match file for the default radiologist, default body part and default x-ray projection, and extracting from said match file said one or more versions with edge enhancement and tonescale image processing parameters and said one or more destinations for each said versions;

processing said provided x-ray image signal to produce said one or more versions of said provided x-ray image signal, as a function of said edge enhancement and tonescale parameters extracted from said match file for each of said versions; and routing each of said produced versions of said x-ray image signal to said one or more destinations extracted from said file.

2. The method of claim 1 wherein said destinations includes a first destination to which more than one version can be routed and a second destination to which only one version can be routed.

3. The method of claim 2 wherein said providing an x-ray image signal step comprises converting a latent x-ray image signal stored in a storage phosphor into said provided x-ray image signal.

4. The method of claim 2 wherein said first destination is a laser printer which prints said more than one version on a single print media.

* * * * *